United States Patent
Takenaka et al.

(10) Patent No.: US 7,314,738 B2
(45) Date of Patent: Jan. 1, 2008

(54) DNA FOR ENCODING D-HYDANTOIN HYDROLASES, DNA FOR ENCODING N-CARBAMYL-D-AMINO ACID HYDROLASES, RECOMBINANT DNA CONTAINING THE GENES, CELLS TRANSFORMED WITH THE RECOMBINANT DNA, METHODS FOR PRODUCING PROTEINS UTILIZING THE TRANSFORMED CELLS AND METHODS FOR PRODUCING D-AMINO ACIDS

(75) Inventors: Yasuhiro Takenaka, Kanagawa (JP); Ikuo Kira, Kanagawa (JP); Kenzo Yokozeki, Kanagawa (JP)

(73) Assignee: Ajinomoto Co., Inc., Tokyo (JP)

(*) Notice: Subject to any disclaimer, the term of this patent is extended or adjusted under 35 U.S.C. 154(b) by 0 days.

(21) Appl. No.: 11/405,455

(22) Filed: Apr. 18, 2006

(65) Prior Publication Data

US 2006/0183892 A1    Aug. 17, 2006

Related U.S. Application Data

(62) Division of application No. 10/189,389, filed on Jul. 8, 2002, now Pat. No. 7,060,485.

(30) Foreign Application Priority Data

Jul. 10, 2001   (JP) .............................. 2001-209712

(51) Int. Cl.
   *C12P 13/04*   (2006.01)
   *C12N 9/10*    (2006.01)
   *C12N 1/21*    (2006.01)
   *C12N 15/63*   (2006.01)
   *C07H 21/04*   (2006.01)

(52) U.S. Cl. ................... 435/106; 435/193; 435/252.3; 435/252.33; 435/320.1; 536/23.2

(58) Field of Classification Search ............ None
See application file for complete search history.

(56) References Cited

U.S. PATENT DOCUMENTS

| 5,523,224 | A |   | 6/1996  | Burtscher et al. |
| 5,679,571 | A |   | 10/1997 | Burtscher et al. |
| 5,807,710 | A | * | 9/1998  | Galli et al. ............... 435/69.1 |
| 6,566,105 | B1 |  | 5/2003  | Grifantini et al. |
| 6,800,465 | B2 |  | 10/2004 | Politino et al. |
| 2003/0109013 | A1 | | 6/2003 | Takenaka et al. |
| 2003/0113880 | A1 | | 6/2003 | Takenaka et al. |
| 2003/0148472 | A1 | | 8/2003 | Takenaka et al. |
| 2003/0148482 | A1 | | 8/2003 | Takenaka et al. |
| 2006/0183892 | A1 | | 8/2006 | Takenaka et al. |

FOREIGN PATENT DOCUMENTS

| EP | 0 610 517    | 8/1994  |
| EP | 0 677 585    | 10/1995 |
| EP | 0 801 131    | 10/1997 |
| JP | 55-114291    | 9/1980  |
| JP | 56-3034      | 1/1981  |
| JP | 3-19696      | 1/1991  |
| JP | 11-113592    | 4/1999  |
| WO | WO 94/00577  | 1/1994  |

OTHER PUBLICATIONS

U.S. Appl. No. 11/476,572, filed Jun. 29, 2006, Takenaka et al.
U.S. Appl. No. 11/433,467, filed May 15, 2006, Takenaka et al.
U.S. Appl. No. 11/405,455, filed Apr. 18, 2006, Takenaka et al.
U.S. Appl. No. 09/462,472, filed Jan. 14, 2000, Takenaka et al.

* cited by examiner

*Primary Examiner*—Elizabeth Slobodyansky
(74) *Attorney, Agent, or Firm*—Oblon, Spivak, McClelland, Maier & Neustadt, P.C.

(57) ABSTRACT

DNA for encoding a protein having D-hydantoinase activity which has a base sequence represented by Sequence ID No. 1 in the Sequence Listing. DNA for encoding a protein having D-carbamylase activity which has a base sequence represented by Sequence ID No. 3 in the Sequence Listing.

20 Claims, 1 Drawing Sheet

ORF1: D-CARBAMYLASE GENE
ORF2: FUNCTIONALLY UNKNOWN GENE
ORF3: D-HYDANTOINASE GENE

DNA FOR ENCODING D-HYDANTOIN HYDROLASES, DNA FOR ENCODING N-CARBAMYL-D-AMINO ACID HYDROLASES, RECOMBINANT DNA CONTAINING THE GENES, CELLS TRANSFORMED WITH THE RECOMBINANT DNA, METHODS FOR PRODUCING PROTEINS UTILIZING THE TRANSFORMED CELLS AND METHODS FOR PRODUCING D-AMINO ACIDS

CONTINUATION DATA

This application is a Divisional application of application Ser. No. 10/189,389, filed Jul. 8, 2002, now U.S. Pat. No. 7,060,485.

FIELD OF THE INVENTION

The present invention relates to a DNA for encoding D-hydantoin hydrolase ("D-hydantoinase") which is utilized preferably for producing D-amino acid, a DNA for encoding N-carbamyl-D-amino acid hydrolase ("D-carbamylase"), a recombinant DNA containing the gene, a cell transformed with the recombinant DNA, a methods for producing a protein using the transformed cell and producing D-amino acid.

BACKGROUND OF THE INVENTION

In a known method for producing amino acid using an enzyme, a 5-substituted hydantoin compound synthesized chemically at a low cost is employed as a starting material and is decomposed asymmetrically into optically active amino acids. A method for producing optically active amino acid from such a 5-substituted hydantoin compound is important for producing pharmaceuticals, chemical industrial products, food additives and the like.

In a method for producing optically active amino acid from such a 5-substituted hydantoin compound, the following enzymes (1) and (2) are required:

(1) An enzyme which catalyzes an N-carbamylamino acid producing reaction via an action on a 5-hydantoin compound to hydrolyze this compound: hydantoin hydrolase (hydantoinase).

(2) An enzyme which catalyzes an optically active amino acid producing reaction via an action on a resultant N-carbamylamino acid to hydrolyze this compound, N-carbamylamino acid hydrolase (carbamylase).

For producing optically active amino acid from a 5-substituted hydantoin compound describe above, an enzyme which is optically selective for at least one of (1) hydantoinase and (2) carbamylase may be employed, and known methods employ a microbial enzyme system or a microbial enzyme system combined with a chemical reaction system.

Among such known methods, a known method for producing D-amino acid from a 5-substituted hydantoin compound using a D-amino acid producing microorganism or a material containing an enzyme produced by the microorganism employs a *Pseudomonas* microorganism (Japanese Patent Application Publication No. 56-003034) or an *Agrobacterium* microorganism (Japanese Patent Application Laid-open No. 019696). Such a D-amino acid producing microorganism frequently has a hydantoinase activity specific generally to a 5-substituted hydantoin in a D form, and when using a DL-5-substituted hydantoin (5-benzylhydatoin as an example here) as a starting material, the D form is hydrolyzed exclusively to form an N-carbamyl-D-amino acid, which is then hydrolyzed by a D-carbamylase which acts exclusively on the D form, resulting in only an amino acid in the D form (D-phenylalanine as an example here), as shown in the following scheme.

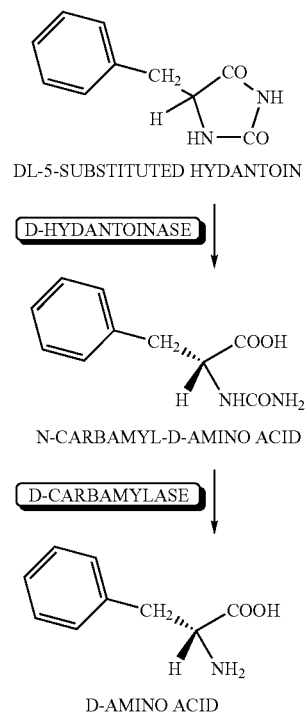

DL-5-SUBSTITUTED HYDANTOIN

D-HYDANTOINASE

N-CARBAMYL-D-AMINO ACID

D-CARBAMYLASE

D-AMINO ACID

SUMMARY OF THE INVENTION

Thus, a production of an optically active amino acid from a 5-substituted hydantoin compound using a cultured cell of a D-amino acid producing microorganism involves here a problem resulting from the need of a derivative such as a hydantoin derivative for the purpose of increasing the production of an enzyme required for the reaction, or the need of a massive amount of the cultured cell.

On the other hand, for the purpose of an efficient production of an optically active amino acid, it is preferable that a D-hydantoinase gene and a D-carbamylase gene are isolated and imparted with an increased gene amplification, transcription and translation to obtain a recombinant whose ability of producing such an enzyme is enhanced, which is then employed in the production. However, a conventional method is problematically time consuming in effecting a reaction, and the reaction allows an N-carbamyl-D-amino acid to be formed as a by-product.

It is an object of the present invention to isolate a D-hydantoinase gene and a D-carbamylase gene from a microorganism having an ability of converting a 5-substituted hydantoin compound to a D-amino acid whereby elucidating the amino acid sequence and the base sequence of an encoding gene and to construct a recombinant whose production of the enzyme is enhanced whereby providing a method for producing the D-amino acid efficiently from the 5-substituted hydantoin.

The present inventors made an effort for solving the problems described above, and were finally successful in isolating a D-hydantoinase gene and a D-carbamylase gene from a microorganism having an ability of converting a 5-substituted hydantoin compound into a D-amino acid, whereby establishing the present invention.

The DNA according to one aspect of the present invention has a base sequence represented by (a) or (b) and that encodes a protein having D-hydantoinase activity, wherein
  (a) is the base sequence represented by Seq. ID No. 1 in the Sequence Listing; and
  (b) is a base sequence hybridizing with a complementary base sequence of the base sequence represented by Seq. ID No. 1 in the Sequence Listing under a stringent condition for encoding.

The DNA according to another aspect of the present invention has an amino acid sequence represented by (c) or (d) and that encodes a protein having D-hydantoinase activity, wherein
  (c) is the amino acid sequence represented by Seq. ID No. 2 in the Sequence Listing;
  (d) is an amino acid sequence resulting from the substitution, deletion, insertion, addition or inversion of one or several amino acid residues in the amino acid sequence represented by Seq. ID No. 2 in the Sequence Listing.

The recombinant DNA according to a third aspect of the present invention results from a connection of a DNA according to the first aspect with a vector DNA.

The recombinant DNA according to a fourth aspect of the present invention results from a connection of a DNA according to the second aspect with a vector DNA.

The cell according to a fifth aspect is transformed with a recombinant DNA according to the third aspect.

The cell according to a sixth aspect is transformed with a recombinant DNA according to the fourth aspect.

The method for producing a protein having D-hydantoinase activity according to a seventh aspect comprises incubating a cell in a culture medium, and allowing a protein having D-hydantoinase activity to be accumulated in one or both of the culture medium and the cell. The cell being the cell according to the fifth aspect.

The method for producing a protein having D-hydantoinase activity according to an eighth aspect comprises incubating a cell in a culture medium, and allowing a protein having D-hydantoinase activity to be accumulated in one or both of the culture medium and the cell. The cell being the cell according to the sixth aspect.

The protein according to a ninth aspect of the present invention has an amino acid sequence represented by (a) or (b) and having D-hydantoinase activity, wherein
  (a) is the amino acid sequence represented by Seq. ID No. 2 in the Sequence Listing; and
  (b) is an amino acid sequence resulting from the substitution, deletion, insertion, addition or inversion of one or several amino acid residues in the amino acid sequence represented by Seq. ID No. 2 in the Sequence Listing.

The method for producing N-carbamyl-D-amino acid according to a tenth aspect of the present invention comprises producing a protein having D-hydantoinase activity by the method according to the seventh aspect, and producing N-carbamyl-D-amino acid by making the protein having D-hydantoinase activity react with a 5-substituted hydantoin. The cell being the cell according to the fifth aspect.

The method for producing N-carbamyl-D-amino acid according to an eleventh aspect of the present invention comprises producing a protein having D-hydantoinase activity by the method according to the eighth aspect, and producing N-carbamyl-D-amino acid by making the protein having D-hydantoinase activity react with a 5-substituted hydantoin. The cell being the cell according to the sixth aspect.

The method for producing D-amino acid according to a twelfth aspect of the present invention comprises producing a protein having D-hydantoinase activity by the method according to the seventh aspect, and producing D-amino acid by making the protein having D-hydantoinase activity and an enzyme hydrolyzing an N-carbamyl-D-amino acid or a material containing the enzyme react with a 5-substituted hydantoin. The cell being the cell according to the fifth aspect.

The method for producing D-amino acid according to a thirteenth aspect of the present invention comprises producing a protein having D-hydantoinase activity by the method according to the eighth aspect, and producing D-amino acid by making the protein having D-hydantoinase activity and an enzyme hydrolyzing an N-carbamyl-D-amino acid or a material containing the enzyme react with a 5-substituted hydantoin. The cell being the cell according to the sixth aspect.

The DNA according to a fourteenth aspect of the present invention has a base sequence represented by (a) or (b) and that encodes a protein having D-carbamylase activity, wherein
  (a) is the base sequence represented by Seq. ID No. 3 in the Sequence Listing; and
  (b) is a base sequence hybridizing with a complementary base sequence of the base sequence represented by Seq. ID No. 3 in the Sequence Listing under a stringent condition.

The DNA according to a fifteenth aspect of the present invention has an amino acid sequence represented by (c) or (d) and that encodes a protein having D-carbamylase activity, wherein
  (c) is the amino acid sequence represented by Seq. ID No. 4 in the Sequence Listing; and
  (b) is an amino acid sequence resulting from the substitution, deletion, insertion, addition or inversion of one or several amino acid residues in the amino acid sequence represented by Seq. ID No. 4 in the Sequence Listing.

The recombinant DNA according to a sixteenth aspect of the present invention results from a connection of the DNA according to the fourteenth aspect with a vector DNA.

The recombinant DNA according to a seventeenth aspect of the present invention results from a connection of the DNA according to the fifteenth aspect with a vector DNA.

The cell according to an eighteenth aspect of the present invention is transformed with a recombinant DNA according to the sixteenth aspect.

The cell according to a nineteenth aspect of the present invention is transformed with a recombinant DNA according to the seventeenth aspect.

The method for producing a protein having D-carbamylase activity according to a twentieth aspect of the present invention comprises incubating a cell in a culture medium, and allowing a protein having D-carbamylase activity to be accumulated in one or both of the culture medium and the cell. The cell being the cell according to the eighteenth aspect.

The method for producing a protein having D-carbamylase activity according to a twenty-first aspect of the present invention comprises incubating a cell in a culture medium, and allowing a protein having D-carbamylase activity to be accumulated in one or both of the culture medium and the cell. The cell being the cell according to the nineteenth aspect.

The protein according to a twenty-second aspect of the present invention has an amino acid sequence represented by (a) or (b) and having D-carbamylase activity, wherein
(a) is the amino acid sequence represented by Seq. ID No. 4 in the Sequence Listing; and
(b) is an amino acid sequence resulting from the substitution, deletion, insertion, addition or inversion of one or several amino acid residues in the amino acid sequence represented by Seq. ID No. 4 in the Sequence Listing.

The method for producing D-amino acid according to a twenty-third aspect of the present invention comprises producing a protein having D-carbamylase activity by the method according to the twentieth aspect, and producing D-amino acid by making the protein having D-carbamylase activity react with an N-carbamylamino acid. The cell being the cell according to the eighteenth aspect.

The method for producing D-amino acid according to a twenty-fourth aspect of the present invention comprises producing a protein having D-carbamylase activity by the method according to the twenty-first aspect, and producing D-amino acid by making the protein having D-carbamylase activity react with an N-carbamylamino acid. The cell being the cell according to the nineteenth aspect.

The method for producing D-amino acid according to a twenty-fifth aspect of the present invention comprises producing a protein having D-carbamylase activity by the method according to the twentieth aspect, and producing D-amino acid by making the protein having D-carbamylase activity and an enzyme hydrolyzing a 5-substituted hydantoin or a material containing the enzyme react with a 5-substituted hydantoin. The cell being the cell according to the eighteenth aspect.

The method for producing D-amino acid according to a twenty-sixth aspect of the present invention comprises producing a protein having D-carbamylase activity by the method according to the twenty-first aspect, and producing D-amino acid by making the protein having D-carbamylase activity and an enzyme hydrolyzing a 5-substituted hydantoin or a material containing the enzyme react with a 5-substituted hydantoin. The cell being the cell according to the nineteenth aspect.

The method for producing D-amino acid according to a twenty-seventh aspect of the present invention comprises producing a protein having D-hydantoinase activity by the method according to the seventh aspect, the cell being the cell according to the fifth aspect, producing a protein having D-carbamylase activity by the method according to the twentieth aspect, the cell being the cell according to the eighteenth aspect, and producing D-amino acid by making the protein having D-hydantoinase activity and the protein having D-carbamylase activity react with a 5-substituted hydantoin.

The method for producing D-amino acid according to a twenty-eighth aspect of the present invention comprises producing a protein having D-hydantoinase activity by the method according to the seventh aspect, the cell being the cell according to the fifth aspect, producing a protein having D-carbamylase activity by the method according to the twenty-first aspect, the cell being the cell according to the nineteenth aspect, and producing D-amino acid by making the protein having D-hydantoinase activity and the protein having D-carbamylase activity react with a 5-substituted hydantoin.

The method for producing D-amino acid according to a twenty-ninth aspect of the present invention comprises producing a protein having D-hydantoinase activity by the method according to the eighth aspect, the cell being the cell according to the sixth aspect, producing a protein having D-carbamylase activity by the method according to the twentieth aspect, the cell being the cell according to the eighteenth aspect, and producing D-amino acid by making the protein having D-hydantoinase activity and the protein having D-carbamylase activity react with a 5-substituted hydantoin.

The method for producing D-amino acid according to a thirtieth aspect of the present invention comprises producing a protein having D-hydantoinase activity by the method according to the eighth aspect, the cell being the cell according to the sixth aspect, producing a protein having D-carbamylase activity by the method according to the twenty-first aspect, the cell being the cell according to the nineteenth aspect, and producing D-amino acid by making the protein having D-hydantoinase activity and the protein having D-carbamylase activity react with a 5-substituted hydantoin.

Other objects and features of this invention will become apparent from the following description with reference to the accompanying drawings.

DETAILED DESCRIPTIONS

Embodiments of the present invention are described below in the order:

[I] DNA for encoding protein having D-hydantoinase activity and protein having D-carbamylase activity,

[II] Method for producing protein having D-hydantoinase activity and protein having D-carbamylase activity, and

[III] Method for producing D-amino acid.

In the following descriptions, a protein having D-hydantoinase activity is sometimes simply referred to as a D-hydantoinase. Moreover, a protein having D-carbamylase activity is sometimes simply referred to as a D-carbamylase.

[I] DNA for Encoding D-hydantoinase and D-carbamylase:

DNAs for encoding D-hydantoinase and D-carbamylase according to the invention is obtained by isolating it from a chromosomal DNA of *Flavobacterium* sp. strain AJ11199 (FERM-P4229) described in Japanese Patent Application Publication No. 56-025119. *Flavobacterium* sp. strain AJ11199 (FERM-P4229) was a microorganism which had initially been deposited under the name of *Alcaligenes aquamarinus* in National Institute of Bioscience and Human-Technology, Ministry of Economy, Trade and Industry, METI, but was subsequently re-identified to be classified in *Flavobacterium* sp. Currently, *Flavobacterium* sp. has been deposited as FERM P-4229 with the Research Institute of Bioscience and Human-technology, AIST, MITY, JAPAN, on Sep. 29, 1977. Later, on May 30, 2002, the same strain has been deposited as FERM BP-8063 based on Budapest convention in the International Patent Organism Depository (IPOD), National Institute of Advanced Industrial Science and Technology (AIST), Japan (Tsukuba City, Higashi 1-1-1, Ibaraki Prefecture, Japan).

The microorganism described above was subjected to physiological and physical tests in accordance with Bergey's Manual of Determinative Bacteriology, Vol. 1 (9th edition, 1994, Williams & Wilkins) which is a text for characterizing microorganisms, and the following results were obtained.

Results of re-identification of *Flavobacterium* sp. strain AJ11199 (FERM-P4229)

| Gram staining | Negative |
|---|---|
| Cell morphology | *Baccilus* |
| Mobility | None |
| Nitrate reduction | – |
| Indole production | – |
| Glucose acidificaiton | – |
| Arginine dihydraze | – |
| Urease | + |
| Esculin hydrolysis | + |
| Gelatin hydrolysis | – |
| β-Galactosidase | + |
| Catalase | + |
| Oxidase | + |
| Substrate catabolyzing ability | |
| Glucose | + |
| L-Arabinose | + |
| D-Mannose | + |
| D-Mannitol | + |
| N-Acetyl-D-glucosamine | + |
| Maltose | + |
| Potassium gluconate | – |
| n-Capric acid | – |
| Adipic acid | – |
| dl-Malic acid | – |
| Sodium citrate | – |
| Phenyl acetate | – |

Based on the bacteriological characteristics described above, AJ11199microorganism was identified as a *Flavobacterium* spp.

Figure 1:
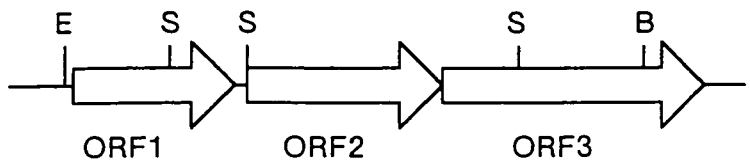
FIG. 1 is a schematic view of the group of the genes encoding the D-hydantoinase and D-carbamylase of strains AJ11199.

The present inventors were successful in obtaining a D-carbamylase gene as being isolated from a gene library prepared using chromosomal DNAs of the AJ11199 microorganism described above. The present inventors also presumed that the downstream base sequence of the gene is an intended D-hydantoinase gene. Thus, as shown in FIG. 1, the D-carbamylase gene and the D-hydantoinase gene derived from the AJ11199 microorganism according to the invention forms a cluster. Accordingly, we were successful in obtaining the entire lengths of the D-hydantoinase gene and D-carbamylase gene of the invention.

The method of a PCR employed for isolating the genes are described for example in White, T. J. et al., Trends Genet. Vol. 5, p. 185, 1989. The methods for preparing a chromosomal DNA and for isolating an intended DNA molecule from a gene library using a DNA molecule as a probe are described for example in Molecular Cloning, 2nd edition, Cold Spring Harbor press (1989).

A method for sequencing a DNA for encoding the isolated D-hydantoinase or D-carbamylase is described for example in A Practical Guide to Molecular Cloning, John Wiley & Sons, Inc. (1985). It is also possible to determine a base sequence using a DNA sequencer manufactured by Applied Biosystems.

In the Sequence Listing attached hereto, the base sequence of the DNA for encoding the D-hydantoinase derived from the AJ11199 microorganism characterized by the method described above is represented by Seq. ID No. 1, while the DNA for encoding the D-carbamylase is represented by Seq. ID No. 3.

Each of these DNAs encodes a protein involved in the production of a D-amino acid.

In the Sequence Listing, Sequence ID No. 2 represents the amino acid sequence of the protein having D-hydantoinase activity encoded by the base sequence of Sequence ID No. 1, while Sequence ID NO. 4 represents the amino acid sequence of the protein having D-carbamylase activity encoded by the base sequence of Sequence ID No. 3.

The protein having the D-hydantoinase activity represented by Sequence ID No. 2 in the Sequence Listing and the protein having the D-carbamylase activity represented by Sequence ID No. 4 in the Sequence Listing catalyze the reactions for forming an optically active amino acid such as D-phenylalanine from a 5-substituted hydantoin such as 5-benzylhydantoin, as shown in the following scheme.

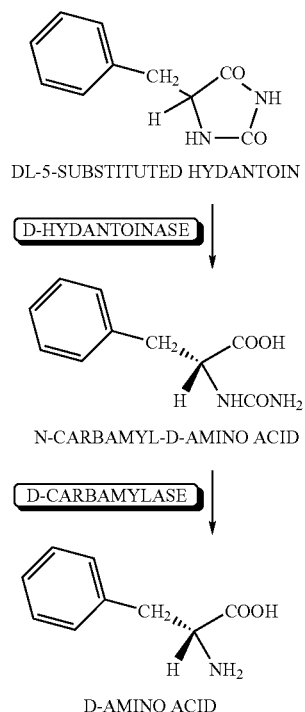

A DNA for encoding a D-hydantoinase according to the invention and a DNA for encoding a D-carbamylase are detailed below.

(1) DNA for Encoding D-Hydantoinase

A D-hydantoinase gene according to the invention which has the base sequence represented by Sequence ID No. 1 in the Sequence Listing is one isolated from a chromosomal DNA of *Flavobacterium* sp. strain AJ11199 as described above, and has the homology of 58% (46% in amino acid sequence) to a known *Agrobacterium* microorganism-derived D-hydantoinase gene (WO96/20275).

The DNA represented by Sequence ID No. 1 in the Sequence Listing DNA is not the only DNA which encodes a D-hydantoinase according to the invention. In other words, the base sequence differs among the species and the strains of *Flavobacterium* microorganisms.

The DNA according to the invention is not only a DNA for encoding the isolated D-hydantoinase but also a DNA resulting from an artificial variation of the DNA for encoding the isolated D-hydantoinase, as a matter of course, as long as a D-hydantoinase is encoded. An artificial variation method employed frequently is a site-specific variation introducing method described for example in Method in Enzymol. P 154, 1987.

The DNA for encoding a protein having D-hydantoinase activity which has a base sequence capable of hybridizing under a stringent condition with a complementary base sequence of the base sequence represented by Sequence ID No. 1 in the Sequence Listing is also a DNA according to the invention. The term "stringent condition" employed here means a condition allowing a specific hybrid to be formed but not allowing a non-specific hybrid to be formed. While it is difficult to specify such a condition as definitive numerical parameters, those which may be exemplified are a condition which allows the DNAs which are highly homologous to each other, preferably have a homology of 70% or higher, more preferably a homology of 90% or higher to each other while not allowing any DNAs having a less homology and a condition of an ordinary southern hybridization washing step, i.e., a hybridization at a salt concentration corresponding to 60° C., 1×SSC, 0.1% SDS, preferably 60° C., 0.1×SSC, 0.1% SDS. The term "D-hydantoinase activity" means any activity capable of producing N-carbamyl-D-amino acid by hydrolyzing a 5-substituted hydantoin compound.

A DNA for encoding a protein which is identical substantially to the D-hydantoinase encoded by the DNA represented by Sequence ID No. 1 in the Sequence Listing is also a DNA according to the invention. Thus, the following (a) or (b) are in the scope of the present invention, where:

(a) is a DNA for encoding the amino acid sequence represented by Seq. ID No. 2 in the Sequence Listing, and (b) is a DNA for encoding a protein having D-hydantoinase activity which has an amino acid sequence resulting from the substitution, deletion, insertion, addition or inversion of one or several amino acid residues in the amino acid sequence represented by Seq. ID No. 2 in the Sequence Listing.

For the purpose of deducing, on the basis of the amino acid sequences (a) and (b) described above, a DNA for encoding such a sequence, a DNA base sequence universal codon can be employed. The term "several" means a number which results in no substantial deterioration of the steric structure or enzymatic activity of the protein, and which is typically 2 to 50, preferably 2 to 30, more preferably 2 to 10. The term "D-hydantoinase activity" means any activity capable of producing N-carbamyl-D-amino acid by hydrolyzing a 5-substituted hydantoin compound. Nevertheless, in the case of a protein involving such a substitution, deletion, insertion, addition or inversion in the amino acid sequence represented by Seq. ID No. 2 in the Sequence Listing, it is preferred that an enzymatic activity which is at least a half of that of the protein having the amino acid sequence represented by Seq. ID No. 2 in the Sequence Listing is possessed.

(2) DNA for Encoding D-Carbamylase

The DNA for encoding the D-carbamylase according to the invention is described below. The D-carbamylase of the present invention having the base sequence represented by Sequence ID No. 3 in the Sequence Listing is isolated from a chromosomal DNA of *Flavobacterium* sp. Strain AJ11199 and has the homology of 78% (79% in amino acid sequence) to a known *Agrobacterium* microorganism-derived D-carbamylase gene (Japanese Patent Publication No. 2902112) and the homology of 67% (58% in amino acid sequence) to a known *Pseudomonas* microorganism-derived D-carbamylase gene (Japanese Patent Publication No. 2902112).

The DNA represented by Sequence ID No. 3 in the Sequence Listing DNA is not the only DNA which encodes the D-carbamylase according to the invention. Thus, the base sequence should differ among the species and the strains of Flavobacterium microorganisms.

A DNA resulting from an artificial variation of the DNA for encoding the isolated D-hydantoinase is also DNA of the present invention as long as it encodes a D-hydantoinase. An artificial variation method employed frequently is a site-specific variation introducing method described for example in Method in Enzymol. P154, 1987.

A DNA for encoding a protein having the D-carbamylase activity which has a base sequence capable of hybridizing under a stringent condition with a complementary sequence of the base sequence represented by Sequence ID No. 3 in the Sequence Listing is also a DNA according to the invention. The term "stringent condition" employed here means a condition allowing a specific hybrid to be formed but not allowing a non-specific hybrid to be formed. While it is difficult to specify such a condition as definitive numerical parameters, those which may be exemplified are a condition which allows the DNAs which are highly homologous to each other, preferably have a homology of 80% or higher, more preferably a homology of 90% or higher to each other while not allowing any DNAs having a less homology and a condition of an ordinary southern hybridization washing step, i.e., a hybridization at a salt concentration corresponding to 60° C., 1×SSC, 0.1% SDS, preferably 60° C., 0.1×SSC, 0.1% SDS. The term "D-carbamylase activity" means any activity capable of producing D-amino acid by hydrolyzing an N-carbamyl-D-amino acid.

A DNA for encoding a protein which is identical substantially to the D-carbamylase encoded by the DNA described above is also a DNA according to the invention. Thus, the following (a) or (b) are in the scope of the present invention, where:

(a) is a DNA for encoding the amino acid sequence represented by Seq. ID No. 4 in the Sequence Listing, (b) is a DNA for encoding a protein having D-hydantoinase activity which has an amino acid sequence resulting from the substitution, deletion, insertion, addition or inversion of one or several amino acid residues in the amino acid sequence represented by Seq. ID No. 4 in the Sequence Listing.

For the purpose of deducing, on the basis of the amino acid sequences (a) and (b) described above, a DNA for encoding such a sequence, a DNA base sequence universal codon can be employed. The term "several" means a number which results in no substantial deterioration of the steric structure or enzymatic activity of the protein, and which is typically 2 to 50, preferably 2 to 30, more preferably 2 to 10. The term "D-carbamylase activity" means any activity capable of producing D-amino acid by hydrolyzing an N-carbamyl-D-amino acid. Nevertheless, in the case of a protein involving such a substitution, deletion, insertion, addition or inversion in the amino acid sequence represented by Seq. ID No. 4 in the Sequence Listing, it is preferred that an enzymatic activity which is at least a half of that of the protein having the amino acid sequence represented by Seq. ID No. 4 in the Sequence Listing is possessed.

[II] Method for Producing D-Hydantoinase and D-Carbamylase:

A method for producing D-hydantoinase and D-carbamylase by a recombinant DNA technology is discussed below. A large number of the methods for producing useful proteins such as enzymes or physiologically active substances utilizing recombinant DNA technologies are known, and a use of the recombinant DNA technology allows a useful protein, which occurs naturally only in a trace amount, to be produced on a large scale.

Figure 2:
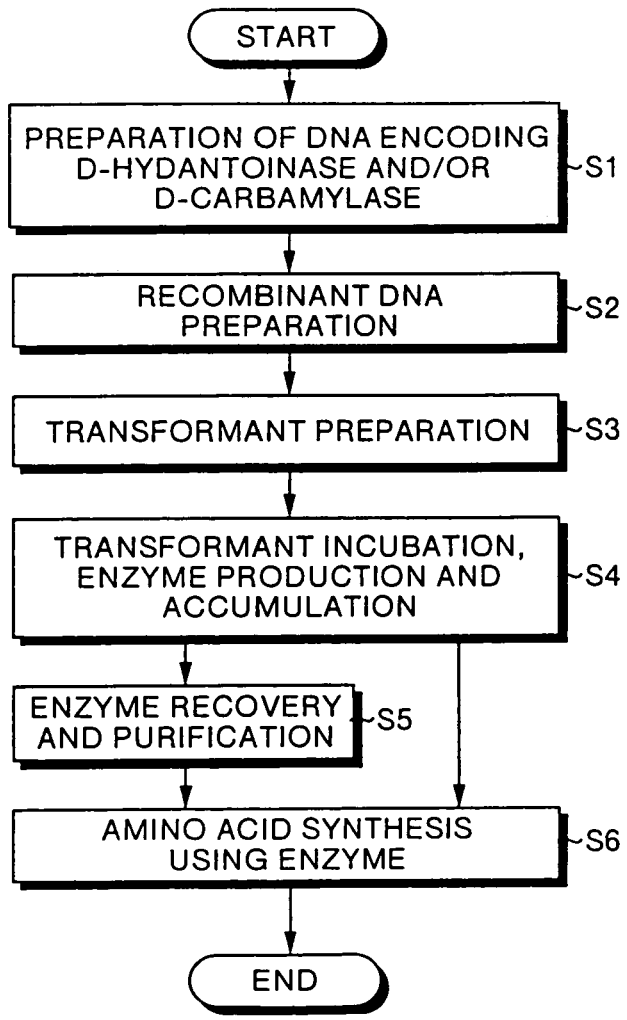
FIG. 2 is a flow chart of a process for producing D-hydantoinase and D-carbamylase according to the invention.

FIG. 2 shows a flow chart of a process for producing D-hydantoinase and D-carbamylase according to the invention.

First, D-hydantoinase DNA of the present invention and/or D-carbamylase DNA are prepared (Step S1).

Then, the prepared NDA is attached to a vector DNA to prepare a recombinant DNA (Step S2), and then a cell is transformed with the recombinant DNA to give a transformant (Step S3). Subsequently, the transformant is incubated in a culture medium to allow the D-hydantoinase and/or D-carbamylase to be produced and accumulated in the culture medium (Step S4).

In the following Step S5, the enzyme is recovered and purified, whereby accomplishing a large scale production of the D-hydantoinase and/or D-carbamylase.

An amino acid synthesis using the enzyme produced in Step S5 and the culture medium of Step S4 in which the enzyme in accumulated enables a large scale production of an intended amino acid (Step S6).

A DNA to be attached to a vector DNA may be anyone allowing a D-hydantoinase of the present invention and/or D-carbamylase to be expressed.

A D-hydantoinase gene employed here to be attached to a vector DNA may for example be those already described above, that is:
  (a) is the DNA having the base sequence represented by Seq. ID No. 1 in the Sequence Listing,
  (b) is the DNA having a base sequence hybridizing with a complementary base sequence of the base sequence represented by Seq. ID No. 1 in the Sequence Listing under a stringent condition,
  (c) is the DNA for encoding the amino acid sequence represented by Seq. ID No. 2 in the Sequence Listing, and
  (d) is the DNA for encoding an amino acid sequence resulting from the substitution, deletion, insertion, addition or inversion of one or several amino acid residues in the amino acid sequence represented by Seq. ID No. 2 in the Sequence Listing.

A D-carbamylase gene employed here to be attached to a vector DNA may for example be those already described above, that is:
  (a) is the DNA having the base sequence represented by Seq. ID No. 3 in the Sequence Listing,
  (b) is the DNA having a base sequence hybridizing with a complementary base sequence of the base sequence represented by Seq. ID No. 3 in the Sequence Listing under a stringent condition,
  (c) is the DNA for encoding the amino acid sequence represented by Seq. ID No. 4 in the Sequence Listing, and
  (d) is the DNA for encoding an amino acid sequence resulting from the substitution, deletion, insertion, addition or inversion of one or several amino acid residues in the amino acid sequence represented by Seq. ID No. 4 in the Sequence Listing.

In addition to the DNAs listed above, a DNA in which a D-hydantoinase gene is ligated to a D-carbamylase may also be employed. In such a case, D-hydantoinase of the present invention and the D-carbamylase of the present invention are expressed simultaneously.

When a recombinant DNA technology is employed to produce a protein on a large scale, a host cell to be transformed may for example be a bacterial cell, actinomyces cell, yeast cell, fungal cell, plant cell, animal cell and the like. Since technologies for producing proteins on large scales using coliform microorganisms have extensively been reported, such a coliform microorganism, especially *Escherichia coli,* is employed generally. A method for producing D-hydantoinase and/or D-carbamylase using a transformed coliform microorganism is discussed below.

A promoter for expressing a DNA for encoding a D-hydantoinase and/or D-carbamylase may be a promoter employed usually for producing a protein in a coliform microorganism, which may for example be a potent promoter such as aT7 promoter, trp promoter, lac promoter, tac promoter, PL promoter and the like.

Also for the purpose of increasing the production, it is preferable to ligate a terminator which is a transcription termination sequence to the downstream of the protein gene. Such a terminator may for example be a T7 terminator, fd phage terminator, T4 terminator, tetracyclin resistant gene terminator, coliform trpA gene terminator and the like.

A vector for transducing a gene encoding a hydantoinase and/or D-carbamylase into a host cell is preferably be one of a multicopy type, such as a plasmid having a replication initiating point derived from Col E1, for example, a pUC plasmid or pBR322 plasmid or a derivative thereof. The term "derivative" employed here is a plasmid which has been subjected to an alteration by the substitution, deletion, insertion, addition or inversion of bases. The alteration referred here means to include an alteration by a mutating treatment using a mutating agent or UV irradiation as well as a spontaneous mutation.

For the purpose of screening for a transformant, the vector having a marker such as an ampicillin resistant gene is employed preferably, such as a plasmid available as an expression vector having a potent promoter, for example, a PUC (Takara Shuzo Co., Ltd.), pPROK (Clonetech), pKK233-2 (Clonetech) and the like.

A DNA fragment in which a promoter, a gene encoding a hydantoinase and/or D-carbamylase and a terminator are ligated in this order is then ligated to a vector DNA to obtain a recombinant DNA.

The recombinant DNA is employed to transform a host cell, and then the cell is incubated, resulting in the expression and production of the hydantoinase and/or D-carbamylase. As a method for effecting a transformation and a method for screening for a transformant, those described in Molecular Cloning, 2nd edition, Cold Spring Harbor press. (1989) are applicable.

As a production medium, a culture medium employed 20 ordinarily for incubating a coliform microorganism such as a M9-casamino acid medium and LB medium may be employed. The incubation condition and the production inducing condition are selected appropriately depending on the types of the marker of the vector, promoter and host cell employed. In order to increase the production of the enzyme, it is also preferred to add isopropyl 1-thio-β-D-galactopyranoside (IPTG) to the culture medium or to conduct an enzyme inducing treatment such as warming.

After recovering a cultured cell for example by a centrifugation, the cell is crushed or subjected to lysis to recover the hydantoinase and/or D-carbamylase, which can be used as a crude enzyme solution. The cell can be crushed by an ultrasonication, French press crushing, glass bead crushing, and the like, or may be subjected to lysis using an albumen lysozyme, peptitase treatment, or a combination thereof. If necessary, the enzyme may be purified by an ordinary procedure such as a precipitation, filtration and column chromatography. In such a case, a purification utilizing an antibody against the enzyme itself can also be utilized.

A D-hydantoinase according to the invention obtained by a recombinant described above is a protein having D-hydantoinase activity which has an amino acid sequence represented by (a) or (b), where:
 (a) is the amino acid sequence represented by Seq. ID No. 2 in the Sequence Listing,
 (b) is the amino acid sequence resulting from the substitution, deletion, insertion, addition or inversion of one or several amino acid residues in the amino acid sequence represented by Seq. ID No. 2 in the Sequence Listing.

A D-carbamylase according to the invention obtained by a recombinant described above is a protein having D-carbamylase activity which has an amino acid sequence represented by (c) or (d), where:
 (c) is the amino acid sequence represented by Seq. ID No. 4 in the Sequence Listing,
 (d) is the amino acid sequence resulting from the substitution, deletion, insertion, addition or inversion of one or several amino acid residues in the amino acid sequence represented by Seq. ID No. 4 in the Sequence Listing.

The definitions of the terms "several", "D-hydantoinase activity" and "D-carbamylase activity" employed here are synonymous with those described in [I] DNA for encoding D-hydantoinase and D-carbamylase.

[III] Method for Producing D-amino Acid

A method for producing D-amino acid employing a hydantoinase and/or D-carbamylase according to the invention is discussed below.

A method for producing D-amino acid according to the invention employs the enzymes of the present invention as at least one of hydantoinase and carbamylase, the combination of which may be one of the three shown below. That is,
 (i) D-hydantoinase of the present invention+ carbamylase,
 (ii) Hydantoinase+ carbamylase of the present invention and
 (iii) D-hydantoinase of the present invention+ carbamylase of the present invention.

In the case of combination (i), a D-hydantoinase may for example be a protein having D-hydantoinase activity which has an amino acid sequence represented by (a) or (b), where:
 (a) is the amino acid sequence represented by Seq. ID No. 2 in the Sequence Listing,
 (b) is the amino acid sequence resulting from the substitution, deletion, insertion, addition or inversion of one or several amino acid residues in the amino acid sequence represented by Seq. ID No. 2 in the Sequence Listing.

It is also possible that a DNA for encoding such a D-hydantoinase is attached to a vector to form a recombinant DNA by which a cell is then transformed and the cell is incubated to yield a D-hydantoinase for use. When a transformed cell is used to produce a D-hydantoinase, a substrate may be added directly to the culture medium during the incubation, or the cell or washed cell recovered from the culture medium may be employed. A cell treatment product obtained by crushing or being subjected to lysis may be employed as it is, or a D-hydantoinase may be recovered from the cell treatment product and used as a crude enzyme solution or may be purified before use. Thus, any fraction containing D-hydantoinase activity can be employed.

A substrate for a D-hydantoinase according to the invention may be any 5-substituted hydantoin compound capable of being hydrolyzed at the substrate specificity of this enzyme. Those which may be exemplified are a 5-substituted hydantoin compound corresponding to a natural amino acid such as hydantoin, 5-methylhydantoin, 5-benzylhydantoin, 5-(4-hydroxybenzyl)hydantoin, 5-indolylmethylhydantoin, 5-(3,4-dihydroxybenzyl)hydantoin, 5-methylthioethylhydantoin, 5-isopropylhydantoin, 5-isobutylhydantoin, 5-sec-butylhydantoin, 5-(4-aminobutyl) hydantoin, 5-hydroxymethylhydantoin and the like, as well as a 5-substituted hydantoin compound corresponding to a non-natural amino acid or a derivative thereof, such as 5-phenylhydantoin, 5-(4-hydroxyphenyl)hydantoin, 5-methoxymethylhydantoin, 5-benzyloxymethylhydantoin, 5-(3,4-methylenedioxybenzyl) hydantoin, dihydrouracil and the like.

A carbamylase to be combined with a D-hydantoinase of the present invention may be any known enzyme capable of catalyzing a reaction which effects hydrolitycally on an N-carbamyl-D-amino acid to yield a D-amino acid or a material containing such an enzyme. Thus, it may be a carbamylase acting specifically on an N-carbamyl-D-amino acid (D-carbamylase) or a non-optically selective carbamylase. The term "material containing an enzyme" employed here means a material containing the enzyme, such as those containing a culture medium, cultured cell, cell treatment product obtained by crushing the cell or subjecting the cell to a lysis, crude enzyme solution or purified enzyme.

A D-carbamylase is known to be present for example in *Pseudomonas* or *Agrobacterium* microorganisms (Japanese Patent 2902112).

Combination (ii) is discussed below. A D-carbamylase of the present invention may for example be a protein having D-carbamylase activity which has an amino acid sequence represented by (a) or (b), where:
 (a) is the amino acid sequence represented by Seq. ID No. 4 in the Sequence Listing,
 (b) is the amino acid sequence resulting from the substitution, deletion, insertion, addition or inversion of one or several amino acid residues in the amino acid sequence represented by Seq. ID No. 4 in the Sequence Listing.

It is also possible that a DNA for encoding such a D-carbamylase is attached to a vector to form a recombinant DNA by which a cell is then transformed and the cell is incubated to yield a D-carbamylase for use. When a transformed cell is used to produce a D-carbamylase, a substrate may be added directly to the culture medium during the incubation, or the cell or washed cell recovered from the culture medium may be employed. A cell treatment product obtained by crushing or being subjected to lysis may be employed as it is, or a D-carbamylase may be recovered from the cell treatment product and used as a crude enzyme solution or may be purified before use. Thus, any fraction containing D-carbamylase activity can be employed.

A substrate for a D-carbamylase according to the invention may be any N-carbamyl-D-amino acid capable of being hydrolyzed at the substrate specificity of this enzyme. Thus, an N-carbamyl-D-amino acid other than the N-carbamyl-D-amino acids obtained from the 5-substituted hydantoin compounds listed above can also be employed as a substrate.

A hydantoinase to be combined with a D-carbamylase of the present invention may be any known enzyme capable of catalyzing a reaction which effects hydrolitycally on a 5-substituted hydantoin compound to yield an N-carbamylamino acid or a material containing such an enzyme. The term "material containing an enzyme" employed here means a material containing the enzyme, such as those containing a culture medium, cultured cell, cell treatment product obtained by crushing the cell or subjecting the cell to a lysis, crude enzyme solution or purified enzyme. Nevertheless, since a D-carbamylase of the present invention is D-form-specific, a non-optically specific hydantoinase or a D-hydantoinase acting specifically on a D form should be employed. A non-optically specific hydantoinase known to be present for example in *Microbacterium* liquefaciens strain AJ3912 (Japanese Patent Application No. 2001-298619). A D-hydantoinase which acts specifically on a hydantoin in the D form is known to be present for example in *Agrobacterium* sp. Strain AJ11220 (Japanese Patent Application Publication No. 56-003034). *Microbacterium* liquefaciens strain AJ3912 was a microorganism which was deposited on Jun. 27, 1975 in National Institute of Bioscience and Human-Technology, Ministry of Economy, Trade and Industry, METI, and received the acceptation number FERM-P3133. Later, on Jun. 27, 2001, the same strain has been deposited as FERM BP-7643 based on Budapest convention. *Agrobacterium* sp. Strain AJ11220 (FERM-P4347) was a microorganism which had initially been deposited under the name of *Pseudomonas* sp. on Dec. 20, 1977 in National Institute of Bioscience and Human-Technology, Ministry of Economy, Trade and Industry, METI, but was subsequently re-identified to be classified in *Agrobacterium* sp. Currently, it is deposited in the International Patent Organism Depositary of National Institute of Advanced Industrial Science and Technology as *Agrobacterium* sp. Strain AJ11220 (National deposit No. FERM-P4347, International deposit No. FERM BP-7645).

In Combination (iii), a D-hydantoinase of the present invention described in the section of Combination (i) and a D-carbamylase of the present invention described in the section of Combination (ii) are combined. Among Combination (I) to (iii), the most preferred combination is Combination (iii).

In the reaction process employed here, a mixture of a D-hydantoinase and D-carbamylase may act on a 5-substituted hydantoin compound, or a D-hydantoinase may first act on a 5-substituted hydantoin compound which is then subjected to the action of a D-carbamylase. The former process is preferred for the purpose of the simplification of the reaction process.

When producing D-amino acid by a method employing any of Combination (i) to (iii) described above, it is possible to produce an N-carbamylamino acid or amino acid in the L form. For example, a D-hydantoinase of the present invention is employed to produce an N-carbamyl-D-amino acid from a DL-5-substituted hydantoin, and then the remaining L-5-substituted hydantoin is separated from the N-carbamyl-D-amino acid to recover the L-5-substituted hydantoin, which is then hydrolyzed to yield an N-carbamyl-L-amino acid, which is further hydrolyzed to yield an L-amino acid. Although such a hydrolyzing reaction may employ a hydrolyzing enzyme acting on an L form, a chemical hydrolyzing treatment for example with nitrous acid also enables the production of an L-amino acid at a high yield with preserving the optical activity.

When converting a DL-5-substituted hydantoin compound into a D-amino acid, the D-amino acid can be produced at a molar yield of 50% or higher from the DL-5-substituted hydantoin compound by means of a combination of the spontaneous racemization or chemical racemization of a 5-substituted hydantoin compound, or the racemization employing a hydantoin racemase.

In other words, it is preferred to use a hydantoin racemase in addition to a D-hydantoinase and D-carbamylase. Such a hydantoin racemase is preferably the hydantoin racemase derived from *Microbacterium* liquefaciens strain AJ3912 (FERM-P3133) described in Japanese Patent Application 2001-278739. In such a case, a D-amino acid can be produced theoretically at 100% molar yield from a DL-5-substituted hydantoin compound since a hydantoin racemase contained in a protein mixture catalyzes the racemization of the 5-substituted hydantoin compound as shown in the following scheme.

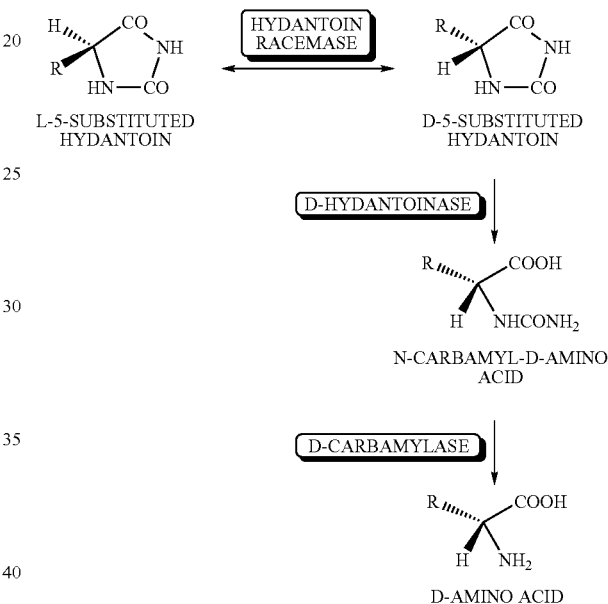

It is also possible to produce an N-carbamylamino acid using the protein mixture described above. For example, the N-carbamylamino acid can be produced by interrupting the hydrolysis reaction at the stage of the N-carbamylamino acid by adding, for example, a D-carbamylase inhibitor to the protein mixture described above.

When an amino acid producing reaction is allowed to proceed using a culture medium of a cell transformed by a recombinant DNA obtained by ligating a DNA for encoding a D-hydantoinase of the present invention and/or D-carbamylase with a vector, isolated cell, washed cell, cell treatment product, crude enzyme solution or purified enzyme solution obtained from the cell treatment product, then a reaction mixture containing the 5-substituted hydantoin compound and the culture medium, isolated cell, washed cell, cell treatment product, crude enzyme solution or purified enzyme solution is kept at an appropriated temperature of 25 to 60° C. at pH 5 to 9 while allowing to stand or stir for 8 hours to 5 days.

When an amino acid producing reaction is allowed to proceed while incubating a cell transformed by a recombinant DNA obtained by ligating a DNA for encoding a D-hydantoinase of the present invention and/or D-carbamylase with a vector in an aqueous medium, an aqueous medium containing a 5-substituted hydantoin compound together with nutrient components essential for the growth of the transformed cell such as carbon sources, nitrogen sources, inorganic ions and the like is employed. The addition of organic trace nutrient components such as vitamins and amino acids may frequently lead to a satisfactory result. It is also possible to add the 5-substituted hydantoin compound in portions. It is preferred to conduct the incubation in an aerobic condition at pH 5 to 9 at an appropriated temperature of 25 to 40° C. for 8 hours to 5 days.

The D-amino acid in a culture medium a reaction mixture can rapidly be quantified by a known method. Thus, for convenience, a thin layer chromatography using for example a HPTLC CHIR manufactured by Merck can be utilized, and, for obtaining a further higher analytical accuracy, a high pressure liquid chromatography (HPLC) employing an optical resolution column such as a CHIRALPAK WH manufactured by DAICEL CHEMICAL INDUSTRIES, LTD. can be employed.

A D-amino acid accumulated in a culture medium or reaction mixture can be collected from the culture medium or reaction mixture by a standard method. For example, procedures such as filtration, centrifugation, concentration under vacuum, ion exchange or adsorption chromatography, crystallization and the like, may be employed if necessary in combination with each other. Especially after converting from a 5-substituted hydantoin compound at a high concentration, the D-amino acid can readily be isolated as a crystal by cooling the culture medium or reaction mixture and adjusting the pH.

The present invention is further described in the following examples, which are not intended to restrict the invention. The quantification and the optical purity assay of a 5-substituted hydantoin compound, N-carbamylamino acid and amino acid in an example are conducted using HPLC employing an optical resolution column, CHIRALPAK WH, manufactured by DAICEL CHEMICAL INDUSTRIES, LTD. The analytical condition is described below.

Column, CHIRALPAK WH 0.46 cmϕ×25cm (DAICEL CHEMICAL INDUSTRIES, LTD.)
Mobile phase: 5% (v/v) Methanol, 1 mM $CuSO_4$
Column temperature: 50° C.
Flow rate: 1.5 ml/min
Detection: $UV_{210}$

EXAMPLE 1

Isolation of D-Hydantoinase Gene and D-Carbamylase Gene from AJ11199 Microorganism 1. Cell Preparation

*Flavobacterium* sp. strain AJ11199 was incubated in a CM2G agar medium (glucose 0.5%, yeast extract 1.0%, peptone 1.0%, NaCl 0.5%, Agar 2%, pH 7.0) at 30° C. for 24 hours, whereby being refreshed. One "spatulaful" of the culture medium was inoculated to a 500 mL Sakaguchi flask containing 50 ml of a CM2G liquid medium, which was then incubated aerobically with shaking at 30° C. for 16 hours.

2. Collection of Chromosomal DNA from Cell 50 ml of the culture medium was centrifuged (12,000×G, 4° C., 15 minutes) and the cell was collected. The cell was then washed by suspending in 10 ml of 50:20 TE (50 mM Tris-HCl, (pH 8.0), 20 mM EDTA) and recovered by centrifugation, and then re-suspended in 10 ml of 50:20 TE. To this suspension, 0.5 ml of a 20 mg/ml lysozyme solution and 1 ml of a 10% SDS solution were added, and the mixture was incubated at 55° C. for 20 minutes. After the incubation, one volume of 10:1 TE-saturated phenol was added to remove proteins. To the separated water layer, one volume of 2-propanol was added to precipitate a DNA for recovery. The precipitated DNA was dissolved in 0.1 ml of 50:20 TE, to which 5 µl of 10 mg/ml RNase and 5 µl of 10 mg/ml Proteinase K were added, and the mixture was reacted at 55° C. for 20 minutes. After the reaction, proteins were removed using one volume of 10:1 TE-saturated phenol. To the separated water layer, one volume of 24:1 chloroform/isoamyl alcohol was added, and the mixture was stirred and then the water layer was recovered. This procedure was repeated twice and then the resultant water layer was supplemented with a 3M sodium acetate solution (pH 5.2) at the final concentration of 0.4 M, and two volumes of ethanol was then added. The precipitated DNA was recovered, washed with 70% ethanol, dried, and then dissolved in 1 ml of 10:1 TE.

3. Isolation of D-Carbamylase from Gene Library

200 µg of the chromosomal DNA of *Flavobacterium* sp. strain AJ11199 was supplemented with 1 U of a restriction enzyme Sau3AI, and the mixture was reacted at 37° C. for 15 minutes to effect a partial digestion. Then, from this DNA 3 to 8 kbp fragments were recovered by an agarose electrophoresis. The fragments were ligated with BamHI digestion products of a plasmid pUC18, whereby transforming an *Esherichia coli* strain JM109 to prepare a gene library. The library was plated onto an ampicillin-supplemented LB medium (tryptone 1%, yeast extract 0.5%, sodium chloride 1%, ampicillin 0.01%, agar 2%, pH 7.0), and then a colony was inoculated in a liquid medium containing as the only nitrogen source N-carbamyl-D-phenylalanine (glucose 0.2%, N-carbamyl-D-phenylalanine 0.2%, $Na_2HPO4$ 0.6%, $KH_2PO_4$ 0.3%, NaCl 0.05%, $MgSO_4$ 0.012%, $CaCl_2$ 0.1 mM, ampicillin 0.01%, thiamine 0.0001%, pH 7.0) to effect an enrichment culture and then a strain capable of growing with N-carbamyl-D-phenylalanine as the only nitrogen source was selected. A transformant thus obtained was isolated and subjected to an incubation on an LB medium containing ampicillin and isopropyl-1-thio-β-D-galactopyranoside (IPTG), followed by centrifugation and cell collection, and then the cell was added at 1% to a 0.1 M phosphate buffer solution containing 0.5% N-carbamyl-D-phenylalanine and allowed to react at 37° C. for 5 hours. The reaction mixture was analyzed and D-phenylalanine was revealed to be produced, whereby assuring that this transformant contained the plasmid containing the intended gene. From this transformant, a plasmid DNA was prepared and designated as pUC632-1.

4. Base Sequence of Inserted Fragment

The base sequence of an inserted fragment of the plasmid pUC632-1 was determined by a dideoxy method. The base sequence of an inserted fragment of the plasmid pUC632-1 is represented by Sequence ID No. 5 in the Sequence Listing. As a result, the length of the inserted fragment was 4.1 kbp and the open reading frame of about 0.9 kb (ORF, Base No. 306 to 1220) which was considered to be a D-carbamylase gene was proven to be contained. This ORF was designated as ORF1. Downstream of ORF1, there was an ORF of about 1.1 kb (Base No. 1287 to 2336), downstream of which an ORF of about 1.5 kb (Base No. 2341 to 3798) was identified. These ORFs were designated as ORF2 and ORF3, respectively (FIG. 1).

5. Homology Between Each Open Reading Frame and Known Sequence

Each ORF thus obtained was characterized for the homology to known sequences, and ORF1 exhibited the homology of 78% (79% in amino acid sequence) to a known *Agrobacterium* microorganism-derived D-carbamylase gene and the homology of 67% (58% in amino acid sequence) to *Pseudomonas* microorganism-derived D-carbamylase gene. ORF3 exhibited the homology of 58% (46% in amino acid sequence) to a known *Agrobacterium* microorganism-derived D-hydantoinase gene. On the other hand, ORF 2 exhibited no homology to known sequences. Based on the results, ORF1 was assumed to be a D-carbamylase gene and ORF3 to be a D-hydantoinase gene. The base sequence of the entire length of the D-hydantoinase gene is represented by Sequence ID No. 1 in the Sequence Listing, while the corresponding amino acid sequence is represented by Sequence ID No. 2 in the Sequence Listing. The base sequence of the entire length of the D-carbamylase gene is represented by Sequence ID No. 3 in the Sequence Listing, while the corresponding amino acid sequence is represented by Sequence ID No. 4 in the Sequence Listing.

EXAMPLE 2

Expression of Strain AJ11199-Derived D-Hydantoinase Gene and D-Carbamylase Gene in *E. coli*

1. Construction of Expression Plasmid

In order to express the both genes in *E. coli*, plasmids pUC632H and pUC632C in which the both genes were ligated to the downstream of the lac promoter of pUC18 were constructed as follows. First, a chromosomal DNA of *Flavobacterium* sp. strain AJ11199 was employed as a template to amplify each gene by a PCR using the oligonucleotides shown in Table 1 as primers. Each of these fragments was digested with XbaI/HindIII and EcoRI/XbaI and ligated to the XbaI/HindIII and EcoRI/XbaI digestion product of pUC18, and then transduced into *E. coli* JM109. The ampicillin resistant strains were screened for strains having intended plasmids, which were designated as expression plasmids pUC632H and pUC632C.

2. Preparation of Cell-Free Extract

Each of an *E. coli* transformant having pUC632H and an *E. coli* transformant having pUC632C was seed-cultured for 16 hours at 37° C. in an LB medium containing 0.1 mg/ml ampicillin. 1 ml of this seed culture was added to a 500 ml Sakaguchi flask containing 50 m of an LB medium, to which 1 ml of the seed culture was added, and the mixture was major-cultured at 37° C. 2.5 hours after initiating the incubation, IPTG was added at the final concentration of 1 mM, and the incubation was continued further for 4 hours.

After completing the incubation, the cells were collected, washed, and suspended in 5 ml of 50 mM KBP (pH 8,0) and crushed using bead heater for 3 minutes (30 seconds×6 cycle, at 90 seconds interval) together with 0.1 mm φ glass beads. The solution was recovered, centrifuged at 20,000 G for 10 minutes, and the supernatant was obtained as a cell-free extract.

3. D-Hydantoinase and D-Carbamylase Activity Assay

The assay of the D-hydantoinase activity was conducted by incubating a reaction mixture containing 120 mg/dl D-5-benzylhydantoin (BH), 50 mM KPB (pH 8.0) and an enzyme solution at 37° C. for 30 minutes, adding 9 volumes of 1.1 mM $CuSO_4$, 11.1 mM $H_3PO_4$, centrifuging at 20,000 G for 10 minutes to remove the pellet, and then quantifying the resultant N-carbamylphenylalanine (N-Car-Phe) by HPLC. One unit of the enzyme activity was defined as an enzymatic activity capable of producing 1 μmol of N-carbamylphenylalanine per 1 minute under the condition described above.

The assay of the D-carbamylase activity was conducted by incubating a reaction mixture containing 80 mg/dl N-carbamyl-D-phenylalanine, 50 mM KPB (pH 7.5) and an enzyme solution at. 37° C. for 30 minutes, adding 9 volumes of 1.1 mM $CuSO_4$, 11.1 mM $H_3PO_4$, centrifuging at 20,000 G for 10 minutes to remove the pellet, and then quantifying the resultant N-phenylalanine (D-Phe) by HPLC. One unit of the enzyme activity was defined as an enzymatic activity capable of producing 1 μmol of N-phenylalanine per 1 minute under the condition described above.

The results are shown in Table 2. Since the strain transformed by pUC632H exhibited D-hydantoinase activity and the strain transformed by pUC632C exhibited D-carbamylase activity, it was proven that the both genes were a D-hydantoinase gene and D-carbamylase gene derived from *Flavobacterium* sp. Strain AJ11199 and were expressed in the cell of *E. coli*.

TABLE 1

Primers employed for amplifying D-hydantoinase gene and D-carbamylase gene derived from strain AJ11199

Hydantoinase 5'-end CGC<u>TCTAGA</u>TAGCCGGAGCTGATACC<u>ATGA</u>  Sequence ID No. 6
                      XbaI                    Initiation codon 3'-end CGC<u>AAGCTTT</u>CCGCC<u>TCA</u>GGCCGTTTCCA  Sequence ID No. 7
                      HindIII   Termination codon Carbamylase  5'-end CGC<u>GAATTC</u>TATCTCGGCGGTTGAGGCTC  Sequence ID No. 8
                      EcoRI 3'-end CGC<u>TCTAGA</u>TGGAGCCGCGCCGC<u>TCA</u>GA  Sequence ID No. 9
                      XbaI              Termination codon

TABLE 2

Enzymatic activity of cell-free extract of *E.coli* having pUC632H and pUC632C

| Plasmid | IPTG supplement | D-Hydantoinase activity (U/mg) | D-Carbamylase activity (U/mg) |
|---|---|---|---|
| pUC632H | + | 0.10 | Not detected |
|  | − | 0.01 | Not detected |
| PUC632C | + | Not detected | 0.12 |
|  | − | Not detected | 0.01 |
| PUC18 | + | Not detected | Not detected |
|  | − | Not detected | Not detected |

EXAMPLE 3

Production of D-Phenylalanine Using Washed *E. Coli* Cell

Washed cells of JM109/pUC632H and JM109/pUC632C incubated similarly to Example 2 were prepared, added each at 1 g/dl to 0.1 mM KPB (pH 7.5) containing 1 g/dl of D-5-benzylhydantoin and reacted at 30° C. By sampling 24 hours after the reaction followed by centrifugation followed by analysis of the supernatant by HPLC, D-phenylalanine produced was quantified.

The results are shown in Table 3. As evident from this table, by using the washed *E. coli* cells in which the D-hydantoinase gene and D-carbamylase gene were expressed, D-phenylalanine was produced efficiently from benzylhydantoine.

TABLE 3

D-Phenylalanine production using washed *E. coli* cells

| D-Hydantoinase gene-expressing strain | D-Carbamylase gene-expressing strain | Phenylalanine production level (g/dl) |
|---|---|---|
| JM109/pUC632H | JM109/pUC632C | 0.33 |
| JM109/pUC18 | JM109/pUC18 | 0.00 |

EXAMPLE 4

Production of D-Amino Acid Using Washed *E. Coli* Cell

Washed cells of JM109/pUC632H and JM109/pUC632C prepared similarly to Example 3 were added each at 1 g/dl to 0.1 mM KPB (pH 7.5) containing 1g/dl of each of 5-substituted hydantoin compounds, and reacted at 30° C. By sampling 24 hours after the reaction followed by centrifugation followed by analysis of the supernatant by HPLC, the resultant each amino acid was quantified.

The results are shown in Table 4. As evident from this table, by using the washed *E. coli* cells in which the D-hydantoinase gene and D-carbamylase gene were expressed, each D-amino acid was produced efficiently from each 5-substituted hydantoin compound.

TABLE 4

D-Amino acid production using washed *E. coli* cells

| 5-Substituted hydantoin compound | Produced amino acid | Production level (g/dl) |
|---|---|---|
| D-5-(4-Hydroxybenzyl)hydantoin | D-Tyrosine | 0.35 |
| D-5-Indolylmethylhydantoin | D-Tryptophan | 0.26 |
| D-5-Methylthioethylhydantoin | D-Methionine | 0.60 |
| Hydantoin | D-Glycine | 0.17 |
| D-5-Methylhydantoin | D-Alanine | 0.31 |
| D-5-Isopropylhydantoin | D-Valine | 0.39 |
| D-5-Isobutylhydantoin | D-Leucine | 0.23 |
| D-5-sec-Butylhydantoin | D-Isoleucine | 0.22 |
| D-5-(4-Aminobutyl)hydantoin | D-Lysine | 0.22 |
| D-5-Carboxyethylhydantoin | D-Glutamic acid | 0.09 |
| D-5-Phenylhydantoin | D-Phenylglycine | 0.43 |
| D-5-(4-Hydroxyphenyl)hydantoin | D-4-Hydroxyphenyl-glycine | 0.53 |

EXAMPLE 5

D-Phenylalanine Production when Combined with Racemization with Hydantoin Racemase An *E. coli* transformant having a plasmid pUCFHR containing a hydantoin racemase gene derived from *Microbacterium liquefaciens* strain AJ3912 (FERM-P3133) described in Japanese Patent Application No. 2001-278739 was seed-cultured for 16 hours at 37° C. in an LB medium containing 0.1mg/ml of ampicillin. 1 ml of this seed culture was added to a 500 ml Sakaguchi flask containing 50 ml of an LB medium, to which 1 ml of the seed culture was added, and the mixture was major-cultured at 37° C. 2.5 hours after initiating the incubation, IPTG was added at the final concentration of 1 mM, and the incubation was continued further for 4 hours. After completing the incubation, the cell was collected, washed, whereby preparing a washed cell.

On the other hand, washed cells of JM109/pUC632H and JM109/pUC632C were prepared similarly to Example 3, added each at 1 g/dl, together with the washed cell of the hydantoin racemase-expressing strain described above, to 0.1 mM KPB (pH 7.5) containing 1 g/dl of DL-5-benzyl-hydantoin and reacted at 30° C. By sampling at 24, 48 and 72 hours after the reaction followed by centrifugation followed by analysis of the supernatant by HPLC, D-phenylalanine produced was quantified.

The results are shown in Table 5. As evident from this table, by using the washed *E. coli* cells in which the hydantoin racemase gene, D-hydantoinase gene and D-carbamylase gene were expressed, D-phenylalanine was produced efficiently from benzylhydantoine in the DL form.

TABLE 5

D-Phenylalanine production when combined with racemization by hydantoin racemase

| Hydantoin racemase gene-expressing strain | D-Hydantoinase gene-expressing strain | D-Carbamylase gene-expressing strain | Phenylalanine production level (g/dl) |
|---|---|---|---|
| JM109/pUCFHR | JM109/pUC632H | JM109/pUC632C | 0.86 |
| JM109/pUC18 | JM109/pUC18 | JM109/pUC18 | 0.00 |

EXAMPLE 6

A Reaction was performed similarly to Example 5 to obtain 500 ml of the reaction solution containing D-phenylalanine. This reaction solution was centrifuged (10,000 G×10 minutes) to separate the cells, and the supernatant was concentrated under reduced pressure to 20 ml, whereby precipitating a crystal of D-phenylalanine. The precipitated crystal was recovered by filtration through a paper filter to obtain a crude crystal. The crude crystal (2.4 g) was dissolved by combining with 10 ml of water and 1 ml of concentrated sulfuric acid, to which 100 mg of activated carbon was added to decolorize the solution. Then, the activated carbon was filtered off, and the filtrate was combined with 5 ml of a 28% aqueous ammonia to adjust at pH 3.5, whereby precipitating D-phenylalanine. Subsequently, the precipitated crystal was recovered by filtration through a filter paper and dried to yield 1.8 g of D-phenylalanine. An HPLC analysis revealed that the material purity was 99% and the optical purity was 99% e.e. or higher.

According to the invention, a D-hydantoinase gene and D-carbamylase gene can be expressed stably in a large amount in a host cell such as a coliform microorganism. As a result, such an enzyme can readily be prepared using such a transformant, resulting in an ability of producing D-amino acid useful in pharmaceuticals, chemical industrial products and food additives efficiently using such a transformant, extract therefrom as well as a purified enzyme and the like.

Although the invention has been described with respect to a specific embodiment for a complete and clear disclosure, the appended claims are not to be thus limited but are to be construed as embodying all modifications and alternative constructions that may occur to one skilled in the art which fairly fall within the basic teaching herein set forth.

What is claimed is:

1. An isolated DNA having a nucleotide sequence comprising (a) or (b) and that encodes a protein having D-carbamylase activity, wherein
   (a) is the nucleotide sequence of SEQ ID NO:3; and
   (b) is a nucleotide sequence hybridizing with the complementary nucleotide sequence of the full length sequence of SEQ ID NO:3 at a salt concentration corresponding of 0.1×SSC, 0.1% SDS at 60° C.

2. An isolated DNA encoding an amino acid sequence of (c) or (d) and that encodes a protein having D-carbamylase activity, wherein
   (c) is the amino acid sequence of SEQ ID NO:4; and
   (d) is an amino acid sequence resulting from the substitution, deletion, insertion or addition of one to 10 amino acid residues in the amino acid sequence of SEQ ID NO:4, wherein the enzymatic activity of the protein having said amino acid sequence is at least half of the activity of the protein having the amino acid sequence of SEQ ID NO:4.

3. A recombinant DNA resulting from a connection of a DNA with a vector DNA, wherein
   the DNA having a nucleotide sequence comprising (a) or (b) and that encodes a protein having D-carbamylase activity, wherein
   (a) is the nucleotide sequence of SEQ ID NO:3; and
   (b) is a nucleotide sequence hybridizing with the complementary nucleotide sequence of the full length sequence of SEQ ID NO:3 at a salt concentration corresponding of 0.1×SSC, 0.1% SDS at 60° C.

4. The recombinant DNA according to claim 3, wherein the vector DNA is derived from a pUC plasmid, pBR322 plasmid or a derivative thereof.

5. A recombinant DNA resulting from a connection of a DNA with a vector DNA, wherein
the DNA encoding an amino acid sequence of (c) or (d) and that encodes a protein having D-carbamylase activity, wherein
(c) is the amino acid sequence of SEQ ID NO:4; and
(d) is an amino acid sequence resulting from the substitution, deletion, insertion, or addition of one to 10 amino acid residues in the amino acid sequence of SEQ ID NO:4, wherein the enzymatic activity of the protein having said amino acid sequence is at least half of the protein having the amino acid sequence of SEQ ID NO:4.

6. The recombinant DNA according to claim 5, wherein the vector DNA is derived from a pUC plasmid, pBR322 plasmid or a derivative thereof.

7. A cell transformed with a recombinant DNA resulting from a connection of a DNA with a vector DNA, wherein
the DNA having a nucleotide sequence comprising (a) or (b) and that encodes a protein having D-carbamylase activity, wherein
(a) is the nucleotide sequence of SEQ ID NO:3; and
(b) is a nucleotide sequence hybridizing with the complementary nucleotide sequence of the full length sequence of SEQ ID NO:3; at a salt concentration corresponding of 0.1×SSC, 0.1% SDS at 60° C.

8. The cell according to claim 7, wherein the cell is an *Escherichia coli*.

9. A cell transformed with a recombinant DNA resulting from a connection of a DNA with a vector DNA, wherein
the DNA encoding an amino acid sequence of (c) or (d) and that encodes a protein having D-carbamylase activity, wherein
(c) is the amino acid sequence of SEQ ID NO:4; and
(d) is an amino acid sequence resulting from the substitution, deletion, insertion, or addition of one to 10 amino acid residues in the amino acid sequence of SEQ ID NO:4, wherein the enzymatic activity of the protein having said amino acid sequence is at least half of the activity of the protein having the amino acid sequence of SEQ ID NO:4.

10. The cell according to claim 9, wherein the cell is an *Escherichia coli*.

11. A method for producing a protein having D-carbamylase activity, the method comprising:
incubating a cell in a culture medium; and
allowing a protein having D-carbamylase activity to be accumulated in one or both of the culture medium and the cell, wherein
the cell to be incubated being transformed with a recombinant DNA resulting from a connection of a DNA with a vector DNA, wherein
the DNA having a nucleotide sequence comprising (a) or (b) and that encodes a protein having D-carbamylase activity, wherein
(a) is the nucleotide sequence of SEQ ID NO:3; and
(b) is a nucleotide sequence hybridizing with the complementary nucleotide sequence of the full sequence of SEQ ID NO:3 at a salt concentration corresponding of 0.1×SSC, 0.1% SDS at 60° C.

12. A method for producing a protein having D-carbamylase activity, the method comprising:
incubating a cell in a culture medium; and
allowing a protein having D-carbamylase activity to be accumulated in one or both of the culture medium and the cell, wherein
the cell to be incubated being transformed with a recombinant DNA resulting from a connection of a DNA with a vector DNA, wherein
the DNA encoding an amino acid sequence of (c) or (d) and that encodes a protein having D-carbamylase activity, wherein
(c) is the amino acid sequence of SEQ ID NO:4; and
(d) is an amino acid sequence resulting from the substitution, deletion, insertion, or addition of one to 10 amino acid residues in the amino acid sequence of SEQ ID NO:4, wherein the enzymatic activity of the protein having said amino acid sequence is at least half of the activity of the protein having the amino acid sequence of SEQ ID NO:4.

13. A method for producing D-amino acid, the method comprising:
producing a protein having D-carbamylase activity by incubating a cell in a culture medium; and
allowing a protein having D-carbamylase activity to be accumulated in one or both of the culture medium and the cell; and
producing D-amino acid by making the protein having D-carbamylase activity react with an N-carbamylamino acid, wherein
the cell to be incubated being transformed with a recombinant DNA resulting from a connection of a DNA with a vector DNA, wherein
the DNA having a nucleotide sequence comprising (a) or (b) and that encodes a protein having D-carbamylase activity, wherein
(a) is the nucleotide sequence of SEQ ID NO:3; and
(b) is a nucleotide sequence hybridizing with the complementary nucleotide sequence of the full length sequence of SEQ ID NO:3 at a salt concentration corresponding of 0.1×SSC, 0.1% SDS at 60° C.

14. The method according to claim 13, wherein an enzyme racemizing a 5-substituted hydantoin compound or a material containing the enzyme is allowed to react with a 5-substituted hydantoin compound to racemize the 5-substituted hydantoin compound.

15. A method for producing D-amino acid, the method comprising:
producing a protein having D-carbamylase activity by incubating a cell in a culture medium; and
allowing a protein having D-carbamylase activity to be accumulated in one or both of the culture medium and the cell; and
producing D-amino acid by making the protein having D-carbamylase activity react with an N-carbamylamino acid, wherein
the cell to be incubated being transformed with a recombinant DNA resulting from a connection of a DNA with a vector DNA, wherein
the DNA encoding an amino acid sequence of (c) or (d) and that encodes a protein having D-carbamylase activity, wherein
(c) is the amino acid sequence of SEQ ID NO:4; and
(d) is an amino acid sequence resulting from the substitution, deletion, insertion, or addition of one to 10 amino acid residues in the amino acid sequence of SEQ ID NO:4, wherein the enzymatic activity of the protein having said amino acid sequence is at least half of the activity of the protein having the amino acid sequence of SEQ ID NO:4.

16. The method according to claim 15, wherein an enzyme racemizing a 5-substituted hydantoin compound or a material containing the enzyme is allowed to react with a 5-substituted hydantoin compound to racemize the 5-substituted hydantoin compound.

17. A method for producing D-amino acid, the method comprising:
producing a protein having D-carbamylase activity by incubating a cell in a culture medium; and
allowing a protein having D-carbamylase activity to be accumulated in one or both of the culture medium and the cell; and
producing D-amino acid by making the protein having D-carbamylase activity and an enzyme hydrolyzing a 5-substituted hydantoin or a material containing the enzyme react with a 5-substituted hydantoin, wherein
the cell to be incubated being transformed with a recombinant DNA resulting from a connection of a DNA with a vector DNA, wherein
the DNA having a nucleotide sequence comprising (a) or (b) and that encodes a protein having D-carbamylase activity, wherein
(a) is the nucleotide sequence of SEQ ID NO:3; and
(b) is a nucleotide sequence hybridizing with the complementary nucleotide sequence of the full length of SEQ ID NO:3 at a salt concentration corresponding of 0.1×SSC, 0.1% SDS at 60° C.

18. The method according to claim 17, wherein an enzyme racemizing a 5-substituted hydantoin compound or a material containing the enzyme is allowed to react with the 5-substituted hydantoin to racemize the 5-substituted hydantoin compound.

19. A method for producing D-amino acid, the method comprising:
producing a protein having D-carbamylase activity by incubating a cell in a culture medium; and
allowing a protein having D-carbamylase activity to be accumulated in one or both of the culture medium and the cell; and
producing D-amino acid by making the protein having D-carbamylase activity and an enzyme hydrolyzing a 5-substituted hydantoin or a material containing the enzyme react with a 5-substituted hydantoin, wherein
the cell to be incubated being transformed with a recombinant DNA resulting from a connection of a DNA with a vector DNA, wherein
the DNA encoding an amino acid sequence of (c) or (d) and that encodes a protein having D-carbamylase activity, wherein
(c) is the amino acid sequence of SEQ ID NO:4; and
(d) is an amino acid sequence resulting from the substitution, deletion, insertion, or addition of one to 10 or several amino acid residues in the amino acid sequence of SEQ ID NO:4, wherein the enzymatic activity of the protein having said amino acid sequence is at least half of the activity of the protein having the amino acid sequence of SEQ ID NO:4.

20. The method according to claim 19, wherein an enzyme racemizing a 5-substituted hydantoin compound or a material containing the enzyme is allowed to react with the 5-substituted hydantoin to racemize the 5-substituted hydantoin compound.

* * * * *

SEQUENCE LISTING

```
<160> NUMBER OF SEQ ID NOS: 9

<210> SEQ ID NO 1
<211> LENGTH: 1458
<212> TYPE: DNA
<213> ORGANISM: Flavobacterium sp.
<220> FEATURE:
<221> NAME/KEY: CDS
<222> LOCATION: (1)..(1455)
<223> OTHER INFORMATION:

<400> SEQUENCE: 1 atg acc cat tac gat ctc gtc att cgc gga gga acc gtc gcc acg gcg      48
Met Thr His Tyr Asp Leu Val Ile Arg Gly Gly Thr Val Ala Thr Ala
1               5                   10                  15 agt gat tgc ttc cgg gcg gat gtt gcg gtc acc gac ggc agg atc gtc      96
Ser Asp Cys Phe Arg Ala Asp Val Ala Val Thr Asp Gly Arg Ile Val
            20                  25                  30 gcc atc ggc gag aat ctc ggg ccc gcc gcc cgc gag atc tcg gcg gaa     144
Ala Ile Gly Glu Asn Leu Gly Pro Ala Ala Arg Glu Ile Ser Ala Glu
        35                  40                  45 ggc cgc ctc gtt ctg ccc ggc ggc gtc gat tcc cat tgc cat atc gag     192
Gly Arg Leu Val Leu Pro Gly Gly Val Asp Ser His Cys His Ile Glu
    50                  55                  60 gag ccg cag gtc ggc gag gtg cgc aac gcg gaa acc ttc gcc tcc gcc     240
Glu Pro Gln Val Gly Glu Val Arg Asn Ala Glu Thr Phe Ala Ser Ala
65                  70                  75                  80 acc tct tcg gcg gcc gcg ggc ggc acg acg acg gtc att tcc ttc tct     288
Thr Ser Ser Ala Ala Ala Gly Gly Thr Thr Thr Val Ile Ser Phe Ser
                85                  90                  95 cag cag gtg aaa ggc ggc ggc atc acc gag gcc ctg cgc gac tat cac     336
Gln Gln Val Lys Gly Gly Gly Ile Thr Glu Ala Leu Arg Asp Tyr His
            100                 105                 110 gag aag gcg acc cgc gcg ctg atc gac tat tcc ttc cat ctc gtc gtg     384
Glu Lys Ala Thr Arg Ala Leu Ile Asp Tyr Ser Phe His Leu Val Val
        115                 120                 125 acc gat ccc acg gat gcg gtg ctg gag gaa ctg gtg ccg ctg atc gag     432
Thr Asp Pro Thr Asp Ala Val Leu Glu Glu Leu Val Pro Leu Ile Glu
    130                 135                 140 gaa ggg cac cgg tcg ctg aag atc ttc atg acc tat acc aat gtc gtg     480
Glu Gly His Arg Ser Leu Lys Ile Phe Met Thr Tyr Thr Asn Val Val
145                 150                 155                 160 ctc gac gac gag cag acg ctg cgc gtg ctg gcg ctc gcc cgc aag acc     528
```

```
                Leu Asp Asp Glu Gln Thr Leu Arg Val Leu Ala Leu Ala Arg Lys Thr
                            165                 170                 175 ggc gct ctc gtc acg gtg cat gcc gag aac cat gcc gcg atc atg tac       576
Gly Ala Leu Val Thr Val His Ala Glu Asn His Ala Ala Ile Met Tyr
            180                 185                 190 ctc acg cgt gcc ttg gaa aag gcc ggg ctc acc gcc ccg aag tac cac       624
Leu Thr Arg Ala Leu Glu Lys Ala Gly Leu Thr Ala Pro Lys Tyr His
        195                 200                 205 gcc tgg gcc aag ccc atg ccg gtg gaa cgg gag gcc tgc cac cgc atc       672
Ala Trp Ala Lys Pro Met Pro Val Glu Arg Glu Ala Cys His Arg Ile
    210                 215                 220 atc atg ctc tcc gaa ctg ctg gat gtt ccc att cag atc ttc cac gtt       720
Ile Met Leu Ser Glu Leu Leu Asp Val Pro Ile Gln Ile Phe His Val
225                 230                 235                 240 tcc ggg gcg gag gcg gcc gag gaa atc cgc cgc gcg cag aat cgc ggc       768
Ser Gly Ala Glu Ala Ala Glu Glu Ile Arg Arg Ala Gln Asn Arg Gly
                245                 250                 255 ctc aag gtc ttc ggc gag acc tgc ccg caa tat ctg atg ctg acg gcg       816
Leu Lys Val Phe Gly Glu Thr Cys Pro Gln Tyr Leu Met Leu Thr Ala
            260                 265                 270 gcg gat ctc gac cgg ccg gat ttc gag ggt gcg aaa ttc ctg tgc agc       864
Ala Asp Leu Asp Arg Pro Asp Phe Glu Gly Ala Lys Phe Leu Cys Ser
        275                 280                 285 ccc gcg ccg cgc acg acg gcc gat cag gaa gcc ctg tgg gac tat atc       912
Pro Ala Pro Arg Thr Thr Ala Asp Gln Glu Ala Leu Trp Asp Tyr Ile
    290                 295                 300 cgc acg gga acg atc ggg gtc gtg tcg tcc gac cac gcg ccg aac cgc       960
Arg Thr Gly Thr Ile Gly Val Val Ser Ser Asp His Ala Pro Asn Arg
305                 310                 315                 320 ttc gac gat ccg cac ggc aag aag gtc ggc ggg gtg gac gcg ccc ttc      1008
Phe Asp Asp Pro His Gly Lys Lys Val Gly Gly Val Asp Ala Pro Phe
                325                 330                 335 agc gcc att ccg aac ggc gtg ccg ggg ctg gcg acg cgc ctg ccg atc      1056
Ser Ala Ile Pro Asn Gly Val Pro Gly Leu Ala Thr Arg Leu Pro Ile
            340                 345                 350 ctg ttt tcc gaa ggg gtc gtc aag ggg cgc atc gac ctc aac acc ttc      1104
Leu Phe Ser Glu Gly Val Val Lys Gly Arg Ile Asp Leu Asn Thr Phe
        355                 360                 365 gtc gcg ctg acg gcg gcc aat ccg gcg aag ctc ttt ggc ctg cat ccc      1152
Val Ala Leu Thr Ala Ala Asn Pro Ala Lys Leu Phe Gly Leu His Pro
    370                 375                 380 aga aag ggc acc atc gcc gtc gga gcc gat gcg gat atc gcg atc tgg      1200
Arg Lys Gly Thr Ile Ala Val Gly Ala Asp Ala Asp Ile Ala Ile Trp
385                 390                 395                 400 gat ccc gag cgc aag gtg acg atc cgc aac gac atg ctg cat cac ggc      1248
Asp Pro Glu Arg Lys Val Thr Ile Arg Asn Asp Met Leu His His Gly
                405                 410                 415 gtc gac tac acg gtc tac gag ggc gtc gag gtg acc gga tgg ccg gtg      1296
Val Asp Tyr Thr Val Tyr Glu Gly Val Glu Val Thr Gly Trp Pro Val
            420                 425                 430 atg acg ctc tcg cgc ggc gag gtg gtc tat gat gac ggc gcg gtg gtc      1344
Met Thr Leu Ser Arg Gly Glu Val Val Tyr Asp Asp Gly Ala Val Val
        435                 440                 445 ggc aag ccg ggt cac ggg cgc ttc ctt gcc cgc ggt ccc tat gac gcg      1392
Gly Lys Pro Gly His Gly Arg Phe Leu Ala Arg Gly Pro Tyr Asp Ala
    450                 455                 460 atc aag ccg cgc ggc agg cat gtg acg cct ttc gac ccg gtg acg ggc      1440
Ile Lys Pro Arg Gly Arg His Val Thr Pro Phe Asp Pro Val Thr Gly
465                 470                 475                 480
```

```
gaa gtg gaa acg gcc tga                                                1458
Glu Val Glu Thr Ala
            485
```

<210> SEQ ID NO 2
<211> LENGTH: 485
<212> TYPE: PRT
<213> ORGANISM: Flavobacterium sp.

<400> SEQUENCE: 2

```
Met Thr His Tyr Asp Leu Val Ile Arg Gly Thr Val Ala Thr Ala
1               5                   10                  15

Ser Asp Cys Phe Arg Ala Asp Val Ala Val Thr Asp Gly Arg Ile Val
                20                  25                  30

Ala Ile Gly Glu Asn Leu Gly Pro Ala Arg Glu Ile Ser Ala Glu
            35                  40                  45

Gly Arg Leu Val Leu Pro Gly Gly Val Asp Ser His Cys His Ile Glu
    50                  55                  60

Glu Pro Gln Val Gly Glu Val Arg Asn Ala Glu Thr Phe Ala Ser Ala
65                  70                  75                  80

Thr Ser Ser Ala Ala Ala Gly Gly Thr Thr Thr Val Ile Ser Phe Ser
                85                  90                  95

Gln Gln Val Lys Gly Gly Ile Thr Glu Ala Leu Arg Asp Tyr His
                100                 105                 110

Glu Lys Ala Thr Arg Ala Leu Ile Asp Tyr Ser Phe His Leu Val Val
            115                 120                 125

Thr Asp Pro Thr Asp Ala Val Leu Glu Glu Leu Val Pro Leu Ile Glu
        130                 135                 140

Glu Gly His Arg Ser Leu Lys Ile Phe Met Thr Tyr Thr Asn Val Val
145                 150                 155                 160

Leu Asp Asp Glu Gln Thr Leu Arg Val Leu Ala Leu Ala Arg Lys Thr
                165                 170                 175

Gly Ala Leu Val Thr Val His Ala Glu Asn His Ala Ala Ile Met Tyr
            180                 185                 190

Leu Thr Arg Ala Leu Glu Lys Ala Gly Leu Thr Ala Pro Lys Tyr His
        195                 200                 205

Ala Trp Ala Lys Pro Met Pro Val Glu Arg Glu Ala Cys His Arg Ile
    210                 215                 220

Ile Met Leu Ser Glu Leu Leu Asp Val Pro Ile Gln Ile Phe His Val
225                 230                 235                 240

Ser Gly Ala Glu Ala Ala Glu Ile Arg Arg Ala Gln Asn Arg Gly
                245                 250                 255

Leu Lys Val Phe Gly Glu Thr Cys Pro Gln Tyr Leu Met Leu Thr Ala
            260                 265                 270

Ala Asp Leu Asp Arg Pro Asp Phe Glu Gly Ala Lys Phe Leu Cys Ser
        275                 280                 285

Pro Ala Pro Arg Thr Thr Ala Asp Gln Glu Ala Leu Trp Asp Tyr Ile
    290                 295                 300

Arg Thr Gly Thr Ile Gly Val Val Ser Ser Asp His Ala Pro Asn Arg
305                 310                 315                 320

Phe Asp Asp Pro His Gly Lys Lys Val Gly Val Asp Ala Pro Phe
                325                 330                 335

Ser Ala Ile Pro Asn Gly Val Pro Gly Leu Ala Thr Arg Leu Pro Ile
            340                 345                 350

Leu Phe Ser Glu Gly Val Val Lys Gly Arg Ile Asp Leu Asn Thr Phe
```

|     |     |     |     |     |     |     |     |     |     |     |     |
| --- | --- | --- | --- | --- | --- | --- | --- | --- | --- | --- | --- |
|     |     | 355 |     |     | 360 |     |     |     | 365 |     |     |
| Val | Ala | Leu | Thr | Ala | Ala | Asn | Pro | Ala | Lys | Leu | Phe | Gly | Leu | His | Pro |
|     | 370 |     |     |     | 375 |     |     |     | 380 |

Arg Lys Gly Thr Ile Ala Val Gly Ala Asp Ala Asp Ile Ala Ile Trp
385                 390                 395                 400

Asp Pro Glu Arg Lys Val Thr Ile Arg Asn Asp Met Leu His His Gly
                405                 410                 415

Val Asp Tyr Thr Val Tyr Glu Gly Val Glu Val Thr Gly Trp Pro Val
            420                 425                 430

Met Thr Leu Ser Arg Gly Glu Val Val Tyr Asp Asp Gly Ala Val Val
            435                 440                 445

Gly Lys Pro Gly His Gly Arg Phe Leu Ala Arg Gly Pro Tyr Asp Ala
        450                 455                 460

Ile Lys Pro Arg Gly Arg His Val Thr Pro Phe Asp Pro Val Thr Gly
465                 470                 475                 480

Glu Val Glu Thr Ala
                485

<210> SEQ ID NO 3
<211> LENGTH: 915
<212> TYPE: DNA
<213> ORGANISM: Flavobacterium sp.
<220> FEATURE:
<221> NAME/KEY: CDS
<222> LOCATION: (1)..(912)
<223> OTHER INFORMATION:

<400> SEQUENCE: 3

```
atg cca gga aag atc att ctc gcg gtg ggc cag ctt gga ccc atc gcc      48
Met Pro Gly Lys Ile Ile Leu Ala Val Gly Gln Leu Gly Pro Ile Ala
1               5                   10                  15 cgc agc gac agc cgc gaa cag gtg gtg aag cgg ctc gtc gac atg ctg      96
Arg Ser Asp Ser Arg Glu Gln Val Val Lys Arg Leu Val Asp Met Leu
                20                  25                  30 gag gag gcc gcg gcc cgc aat tcg gat ttc atc gtc ttt ccc gag ctg     144
Glu Glu Ala Ala Ala Arg Asn Ser Asp Phe Ile Val Phe Pro Glu Leu
            35                  40                  45 gcg ctg acc acc ttc ttc ccc cgc tgg tat ttc acc gac gag gcg gaa     192
Ala Leu Thr Thr Phe Phe Pro Arg Trp Tyr Phe Thr Asp Glu Ala Glu
        50                  55                  60 ctg gac gcg ttc tac gag acg gaa atg ccg agc ccg gtg aca cgc ccg     240
Leu Asp Ala Phe Tyr Glu Thr Glu Met Pro Ser Pro Val Thr Arg Pro
65                  70                  75                  80 ctg ttc gag gcc gcc gcg aaa cac ggc gtc ggg ttc aat ctc ggc ttc     288
Leu Phe Glu Ala Ala Ala Lys His Gly Val Gly Phe Asn Leu Gly Phe
                85                  90                  95 gcg gag ctc gtg tcg gag ggc ggc agg aag cgc cgc ttc aac acg tcc     336
Ala Glu Leu Val Ser Glu Gly Gly Arg Lys Arg Arg Phe Asn Thr Ser
                100                 105                 110 atc gcc gtc gac agg acc ggc agg atc atc ggc aag tac cgc aag atc     384
Ile Ala Val Asp Arg Thr Gly Arg Ile Ile Gly Lys Tyr Arg Lys Ile
            115                 120                 125 cat ctg ccg ggc cac aag gac tat gaa gac tac cgc ccg ttc cag cat     432
His Leu Pro Gly His Lys Asp Tyr Glu Asp Tyr Arg Pro Phe Gln His
        130                 135                 140 ctg gag aag cgg tac ttc gag acc ggc aat ctc gga ttc ccg gtc tat     480
Leu Glu Lys Arg Tyr Phe Glu Thr Gly Asn Leu Gly Phe Pro Val Tyr
145                 150                 155                 160 gag gtc gat ggt ttc aag atg ggc atg ttc atc tgc aac gac cgg cgc     528
Glu Val Asp Gly Phe Lys Met Gly Met Phe Ile Cys Asn Asp Arg Arg
```

-continued

|   |   |   |   |   |   |   |   |   |   |   |   |   |   |   |   |     |
|---|---|---|---|---|---|---|---|---|---|---|---|---|---|---|---|-----|
|   |   |   | 165 |   |   |   | 170 |   |   |   | 175 |   |   |   |   |     |
| tgg | ccg | gag | acc | tgg | cgc | gtg | atg | ggt | ctc | aag | ggc | gcg | gag | ctg | atc | 576 |
| Trp | Pro | Glu | Thr | Trp | Arg | Val | Met | Gly | Leu | Lys | Gly | Ala | Glu | Leu | Ile |     |
|   |   |   | 180 |   |   |   | 185 |   |   |   | 190 |   |   |   |   |     |
| tgc | ggc | ggc | tac | aac | acg | ccg | ctg | cac | aat | ccg | ccg | gtg | ccg | cag | cac | 624 |
| Cys | Gly | Gly | Tyr | Asn | Thr | Pro | Leu | His | Asn | Pro | Pro | Val | Pro | Gln | His |     |
|   |   |   | 195 |   |   |   | 200 |   |   |   | 205 |   |   |   |   |     |
| gac | cag | ctc | agc | tcc | ttc | cac | cat | ctc | ctg | tcg | atg | cag | gcg | ggc | gcc | 672 |
| Asp | Gln | Leu | Ser | Ser | Phe | His | His | Leu | Leu | Ser | Met | Gln | Ala | Gly | Ala |     |
|   |   | 210 |   |   |   | 215 |   |   |   | 220 |   |   |   |   |   |     |
| tac | cag | aac | ggt | gcg | tgg | acc | gcc | gga | gcg | ggc | aag | gtc | ggg | gtg | gag | 720 |
| Tyr | Gln | Asn | Gly | Ala | Trp | Thr | Ala | Gly | Ala | Gly | Lys | Val | Gly | Val | Glu |     |
| 225 |   |   |   | 230 |   |   |   | 235 |   |   |   |   |   |   | 240 |     |
| gaa | ggc | tgc | atg | ctg | ctc | ggc | cat | tcc | tgc | atc | gtc | gcg | ccc | acc | ggg | 768 |
| Glu | Gly | Cys | Met | Leu | Leu | Gly | His | Ser | Cys | Ile | Val | Ala | Pro | Thr | Gly |     |
|   |   |   |   | 245 |   |   |   | 250 |   |   |   | 255 |   |   |   |     |
| gag | ctt | gcc | gcg | ctc | acc | aac | acg | ctg | gag | gac | gag | gtc | atc | acg | gcc | 816 |
| Glu | Leu | Ala | Ala | Leu | Thr | Asn | Thr | Leu | Glu | Asp | Glu | Val | Ile | Thr | Ala |     |
|   |   |   | 260 |   |   |   | 265 |   |   |   | 270 |   |   |   |   |     |
| gct | gcc | gat | ttt | gcc | cgc | tgc | cgg | gaa | atc | cgc | gag | aac | atc | ttc | aat | 864 |
| Ala | Ala | Asp | Phe | Ala | Arg | Cys | Arg | Glu | Ile | Arg | Glu | Asn | Ile | Phe | Asn |     |
|   |   | 275 |   |   |   | 280 |   |   |   | 285 |   |   |   |   |   |     |
| ttc | gag | cag | cat | cgc | gag | ccg | cag | gaa | tac | ggg | ttg | atc | gcc | gcc | gtc | 912 |
| Phe | Glu | Gln | His | Arg | Glu | Pro | Gln | Glu | Tyr | Gly | Leu | Ile | Ala | Ala | Val |     |
|   | 290 |   |   |   | 295 |   |   |   | 300 |   |   |   |   |   |   |     |
| tga |   |   |   |   |   |   |   |   |   |   |   |   |   |   |   | 915 |

<210> SEQ ID NO 4
<211> LENGTH: 304
<212> TYPE: PRT
<213> ORGANISM: Flavobacterium sp.

<400> SEQUENCE: 4

Met Pro Gly Lys Ile Ile Leu Ala Val Gly Gln Leu Gly Pro Ile Ala
1               5                   10                  15

Arg Ser Asp Ser Arg Glu Gln Val Val Lys Arg Leu Val Asp Met Leu
            20                  25                  30

Glu Glu Ala Ala Ala Arg Asn Ser Asp Phe Ile Val Phe Pro Glu Leu
        35                  40                  45

Ala Leu Thr Thr Phe Phe Pro Arg Trp Tyr Phe Thr Asp Glu Ala Glu
    50                  55                  60

Leu Asp Ala Phe Tyr Glu Thr Glu Met Pro Ser Pro Val Thr Arg Pro
65                  70                  75                  80

Leu Phe Glu Ala Ala Lys His Gly Val Gly Phe Asn Leu Gly Phe
                85                  90                  95

Ala Glu Leu Val Ser Glu Gly Gly Arg Lys Arg Phe Asn Thr Ser
            100                 105                 110

Ile Ala Val Asp Arg Thr Gly Arg Ile Gly Lys Tyr Arg Lys Ile
        115                 120                 125

His Leu Pro Gly His Lys Asp Tyr Glu Asp Tyr Arg Pro Phe Gln His
    130                 135                 140

Leu Glu Lys Arg Tyr Phe Glu Thr Gly Asn Leu Gly Phe Pro Val Tyr
145                 150                 155                 160

Glu Val Asp Gly Phe Lys Met Gly Met Phe Ile Cys Asn Asp Arg Arg
                165                 170                 175

Trp Pro Glu Thr Trp Arg Val Met Gly Leu Lys Gly Ala Glu Leu Ile
            180                 185                 190

-continued

```
Cys Gly Gly Tyr Asn Thr Pro Leu His Asn Pro Pro Val Pro Gln His
            195                 200                 205

Asp Gln Leu Ser Ser Phe His His Leu Leu Ser Met Gln Ala Gly Ala
    210                 215                 220

Tyr Gln Asn Gly Ala Trp Thr Ala Gly Ala Gly Lys Val Gly Val Glu
225                 230                 235                 240

Glu Gly Cys Met Leu Leu Gly His Ser Cys Ile Val Ala Pro Thr Gly
                245                 250                 255

Glu Leu Ala Ala Leu Thr Asn Thr Leu Glu Asp Glu Val Ile Thr Ala
            260                 265                 270

Ala Ala Asp Phe Ala Arg Cys Arg Glu Ile Arg Glu Asn Ile Phe Asn
    275                 280                 285

Phe Glu Gln His Arg Glu Pro Gln Glu Tyr Gly Leu Ile Ala Ala Val
    290                 295                 300
```

<210> SEQ ID NO 5
<211> LENGTH: 4054
<212> TYPE: DNA
<213> ORGANISM: Flavobacterium sp.

<400> SEQUENCE: 5

| | | | | | |
|---|---|---|---|---|---|
| gatcggccgc | gcgctgatgt | cgaagccgcg | ccttctgctt | ctcgacgaac | cctcgctggg | 60 |
| actggcgccg | ctcgtcgtgc | gcgacatcgc | ccgtctcgtc | acggagatca | accgggagca | 120 |
| gggcaccagc | atcgtgctgg | tcgagcagaa | ttcgcgcatg | cgctgcgca | tcagccgata | 180 |
| cgcctatgtg | ctcgaaaccg | ggcgcatcgg | tctcgaagga | gcctcgcaga | gcctcctcga | 240 |
| cgacgacaag | gtcaagcaac | tctatctcgg | cggttgaggc | tccgggaaag | gaaaaggaga | 300 |
| ggaatatgcc | aggaaagatc | attctcgcgg | tgggccagct | ggacccatc | gcccgcagcg | 360 |
| acagccgcga | acaggtggtg | aagcggctcg | tcgacatgct | ggaggaggcc | gcggcccgca | 420 |
| attcggattt | catcgtcttt | cccgagctgg | cgctgaccac | cttcttcccc | cgctggtatt | 480 |
| tcaccgacga | ggcggaactg | gacgcgttct | acgagacgga | aatgccgagc | ccggtgacac | 540 |
| gcccgctgtt | cgaggccgcc | gcgaaacacg | gcgtcgggtt | caatctcggc | ttcgcggagc | 600 |
| tcgtgtcgga | gggcggcagg | aagcgccgct | caacacgtc | catcgccgtc | gacaggaccg | 660 |
| gcaggatcat | cggcaagtac | cgcaagatcc | atctgccggg | ccacaaggac | tatgaagact | 720 |
| accgcccgtt | ccagcatctg | gagaagcggt | acttcgagac | cggcaatctc | ggattcccgg | 780 |
| tctatgaggt | cgatggtttc | aagatgggca | tgttcatctg | caacgaccgg | cgctggccgg | 840 |
| agacctggcg | cgtgatgggt | ctcaaggcg | cggagctgat | ctgcggcggc | tacaacacgc | 900 |
| cgctgcacaa | tccgccggtg | ccgcagcacg | accagctcag | ctccttccac | catctcctgt | 960 |
| cgatgcaggc | gggcgcctac | cagaacggtg | cgtggaccgc | cggagcgggc | aaggtcgggg | 1020 |
| tggaggaagg | ctgcatgctg | ctcggccatt | cctgcatcgt | cgcgcccacc | ggggagcttg | 1080 |
| ccgcgctcac | caacacgctg | gaggacgagg | tcatcacggc | cgctgccgat | tttgcccgct | 1140 |
| gccgggaaat | ccgcgagaac | atcttcaatt | tcgagcagca | tcgcgagccg | caggaatacg | 1200 |
| ggttgatcgc | cgccgtctga | gcggcgcggc | tccatacaat | catgatgccc | gagccgcctt | 1260 |
| cctgtgggag | gcgaacggg | caaggcatgc | ccgccggaca | tacggcgggc | ggaggagaaa | 1320 |
| ggagggagac | catgcgcgcg | atcctgctgg | atcagcccgg | cgaagccgcc | ggcctgttgc | 1380 |
| gcgtcgccga | gctgcccgcg | ccggtcgcgg | ggcgcggaga | actcgtcgtc | gcggtcgcct | 1440 |
| gctgcggctg | caacttcgcc | gacacgatga | tgcggcgcgg | tacctatccg | catccgaagc | 1500 |

```
aatacccgct cgttcccggt ttcgagatcg tgggccgggt gacggcggtc ggtgcgggcg    1560
tcgatggttt tgccgtcggc gaccgggtgg cgggctatgc cgagtcgggc ggcggctttg    1620
ccgcgctctg cgccgttgcg gcggacggtg ccgttcgcct tcccgattcc gttcccttcg    1680
aaacggcggc agccttcctc atccaggcgc agacggcctg gcatctgctg cataccgtct    1740
cggcggtgcg accgggtgag gtcgtcctga tccacgccat cggcggcggt gtcgggctct    1800
atctcaccca gctcgccgtg caggccggag ccgtcgttgt cggtaccgtc ggcacggccg    1860
gcaaggaaag gcgggcgctc gattatggcg caagcctcgt cgtcaaccgc gcggaggctg    1920
atttcgtgga ggagatcggc cgcttcctga acgggcgcgg cgtcgacagg atttacgatt    1980
ccaccggggc gacgatcctc gaccgtagct ttgcgctcct gcgcccgctc ggccagatcg    2040
tcagtttcgg cgaggccgag ggccgcccgc tcgacaatct ctgggcgcgg ctggtggaga    2100 atcggcgac cttcacgcgc ttccatctcg gccatctcga tttcgccgcg caagcctggc    2160
gcgacgggct gcgccttacc cttgccgccg tcgcggacgg tacgcttcgc gtgccggtcg    2220
aacgcgtctt ttccttcgaa caggcagagc agatgtatga atgcctcgaa tcccgcacgg    2280
tgtcgggaaa gctcctgctt gccgtcaacc ctaccgcaac cgatagccgg agctgatacc    2340
atgacccatt cgatctcgt cattcgcgga ggaaccgtcg ccacggcgag tgattgcttc    2400
cgggcggatg ttgcggtcac cgacggcagg atcgtcgcca tcggcgagaa tctcgggccc    2460
gccgcccgcg agatctcggc ggaaggccgc ctcgttctgc ccggcggcgt cgattcccat    2520
tgccatatcg aggagccgca gtcggcgag gtgcgcaacg cggaaaacctt cgcctccgcc    2580 acctcttcgg cggccgcggg cggcacgacg acggtcattt ccttctctca gcaggtgaaa    2640
ggcggcggca tcaccgaggc cctgcgcgac tatcacgaga aggcgacccg cgcgctgatc    2700
gactattcct tccatctcgt cgtgaccgat cccacggatg cggtgctgga ggaactggtg    2760
ccgctgatcg aggaagggca ccgtcgctg aagatcttca tgacctatac caatgtcgtg    2820
ctcgacgacg agcagacgct gcgcgtgctg gcgctcgccc gcaagaccgg cgctctcgtc    2880
acggtgcatg ccgagaacca tgccgcgatc atgtacctca cgcgtgcctt ggaaaaggcc    2940
gggctcaccg ccccgaagta ccacgcctgg gccaagccca tgccggtgga acgggaggcc    3000
tgccaccgca tcatcatgct ctccgaactg ctggatgttc ccattcagat cttccacgtt    3060
tccggggcgg aggcggccga ggaaatccgc cgcgcgcaga atcgcggcct caaggtcttc    3120
ggcgagacct gcccgcaata tctgatgctg acggcggcgg atctcgaccg gccggatttc    3180
gagggtgcga aattcctgtg cagccccgcg ccgcgcacga cggccgatca ggaagccctg    3240
tgggactata tccgcacggg aacgatcggg gtcgtgtcgt ccgaccacgc gccgaaccgc    3300
ttcgacgatc cgcacggcaa gaaggtcggc ggggtggacg cgcccttcag cgccattccg    3360 aacgcgtgc cggggctggc gacgcgcctg ccgatcctgt tttccgaagg ggtcgtcaag    3420
gggcgcatcg acctcaacac cttcgtcgcg ctgacgcgcg ccaatccggc gaagctcttt    3480
ggcctgcatc ccagaaaggg caccatcgcc gtcggagccg atgcggatat cgcgatctgg    3540
gatcccgagc gcaaggtgac gatccgcaac gacatgctgc atcacggcgt cgactacacg    3600
gtctacgagg gcgtcgaggt gaccggatgg ccggtgatga cgctctcgcg cggcgaggtg    3660
gtctatgatg acggcgcggt ggtcggcaag ccgggtcacg ggcgcttcct tgcccgcggt    3720
ccctatgacg cgatcaagcc gcgcggcagg catgtgacgc ctttcgaccc ggtgacgggc    3780
gaagtggaaa cggcctgagg cggaaaggac aggacgatga agatcaaggt gatcaatccg    3840
```

```
aacacgacat tgaccatgac cgccaagatc ggcgaggcgg ccgccgccgt cgcctcggcg    3900
ggaaccgagg tcgtcgccgt cagccccgct atggggccgg cctccatcga ggggcattat    3960
gacgaggcgg tcagtgcgct cggcgtgctc gacgaagtgc gcaagggaaa ggcggaagga    4020
tgcgacggct atcttatcgc ctgcttcgac gatc                                4054

<210> SEQ ID NO 6
<211> LENGTH: 30
<212> TYPE: DNA
<213> ORGANISM: Artificial Sequence
<220> FEATURE:
<223> OTHER INFORMATION: synthetic DNA

<400> SEQUENCE: 6
cgctctagat agccggagct gataccatga                                      30

<210> SEQ ID NO 7
<211> LENGTH: 29
<212> TYPE: DNA
<213> ORGANISM: Artificial Sequence
<220> FEATURE:
<223> OTHER INFORMATION: synthetic DNA

<400> SEQUENCE: 7
cgcaagcttt ccgcctcagg ccgtttcca                                       29

<210> SEQ ID NO 8
<211> LENGTH: 29
<212> TYPE: DNA
<213> ORGANISM: Artificial Sequence
<220> FEATURE:
<223> OTHER INFORMATION: synthetic DNA

<400> SEQUENCE: 8
cgcgaattct atctcggcgg ttgaggctc                                       29

<210> SEQ ID NO 9
<211> LENGTH: 28
<212> TYPE: DNA
<213> ORGANISM: Artificial Sequence
<220> FEATURE:
<223> OTHER INFORMATION: synthetic DNA

<400> SEQUENCE: 9
cgctctagat ggagccgcgc cgctcaga                                        28
```